(12) United States Patent
Tchaga

(10) Patent No.: US 7,723,125 B2
(45) Date of Patent: *May 25, 2010

(54) HIGHLY SENSITIVE PROTEOMIC ANALYSIS METHODS, AND KITS AND SYSTEMS FOR PRACTICING THE SAME

(75) Inventor: Grigoriy S. Tchaga, Newark, CA (US)

(73) Assignee: Clontech Laboratories Inc., Mountain View, CA (US)

( * ) Notice: Subject to any disclaimer, the term of this patent is extended or adjusted under 35 U.S.C. 154(b) by 146 days.

This patent is subject to a terminal disclaimer.

(21) Appl. No.: 11/850,474

(22) Filed: Sep. 5, 2007

(65) Prior Publication Data

US 2009/0099032 A1   Apr. 16, 2009

Related U.S. Application Data

(63) Continuation of application No. 09/960,716, filed on Sep. 21, 2001, now Pat. No. 7,354,721.

(60) Provisional application No. 60/234,527, filed on Sep. 22, 2000.

(51) Int. Cl.
    *G01N 33/543* (2006.01)
(52) U.S. Cl. .................................................. 436/518
(58) Field of Classification Search ....................... None
    See application file for complete search history.

(56) References Cited

U.S. PATENT DOCUMENTS

| | | | |
|---|---|---|---|
| 3,791,933 A * | 2/1974 | Moyer et al. ............. 435/287.8 |
| 4,111,656 A * | 9/1978 | Margherita ................. 436/500 |
| 4,514,508 A | 4/1985 | Hirschfeld |
| 4,537,861 A | 8/1985 | Elings et al. |
| 4,541,952 A * | 9/1985 | Hosoi et al. ................. 530/351 |
| 4,591,570 A | 5/1986 | Chang |
| 4,829,010 A | 5/1989 | Chang |
| 4,837,167 A * | 6/1989 | Schoemaker et al. ........... 435/5 |
| 5,021,567 A * | 6/1991 | Johnson et al. ............. 540/470 |
| 5,057,302 A * | 10/1991 | Johnson et al. ............ 424/1.17 |
| 5,100,777 A | 3/1992 | Chang |
| 5,143,854 A | 9/1992 | Pirrung et al. |
| 5,171,695 A | 12/1992 | Ekins |
| 5,328,603 A * | 7/1994 | Velander et al. .......... 210/198.2 |
| 5,432,099 A | 7/1995 | Ekins |
| 5,436,170 A | 7/1995 | Cornell et al. |
| 5,445,934 A | 8/1995 | Fodor et al. |
| 5,486,452 A | 1/1996 | Gordon et al. |
| 5,516,635 A | 5/1996 | Ekins et al. |
| 5,532,128 A | 7/1996 | Eggers et al. |
| 5,556,752 A | 9/1996 | Lockhart et al. |
| 5,599,720 A | 2/1997 | Ekins |
| 5,635,609 A * | 6/1997 | Levy et al. ...................... 536/2 |
| 5,674,698 A * | 10/1997 | Zarling et al. ............. 435/7.92 |
| 5,700,637 A | 12/1997 | Southern |
| 5,747,274 A * | 5/1998 | Jackowski ................. 435/7.94 |
| 5,763,175 A | 6/1998 | Brenner |
| 5,773,227 A * | 6/1998 | Kuhn et al. ................. 435/7.21 |
| 5,773,234 A * | 6/1998 | Pronovost et al. .......... 435/7.36 |
| 5,807,522 A | 9/1998 | Brown et al. |
| 5,863,722 A | 1/1999 | Brenner |
| 5,994,076 A | 11/1999 | Chenchik et al. |
| 6,197,599 B1 | 3/2001 | Chin et al. |
| 6,207,369 B1 * | 3/2001 | Wohlstadter et al. ........... 435/6 |
| 6,255,048 B1 * | 7/2001 | Hosoi et al. ..................... 435/6 |
| 6,261,626 B1 * | 7/2001 | Buchholt et al. ............. 426/577 |
| 6,482,517 B1 * | 11/2002 | Anderson .............. 428/402.24 |
| 7,354,721 B2 * | 4/2008 | Tchaga ....................... 435/7.1 |

FOREIGN PATENT DOCUMENTS

| | | |
|---|---|---|
| WO | WO 88/01058 | 2/1988 |
| WO | WO 89/01157 | 2/1989 |
| WO | WO 97/24455 | 7/1997 |
| WO | WO 98/53103 | 11/1998 |
| WO | WO 99/31267 | 6/1999 |

(Continued)

OTHER PUBLICATIONS

Kartel et al., "Evaluation of Pectin Binding of Heavy Metal Ions inAqueous Solutions", Chemosphere, vol. 38, No. 11, pp. 2591-2596, 1999.*

(Continued)

*Primary Examiner*—Ann Y Lam
(74) *Attorney, Agent, or Firm*—Bret E. Field; Bozicevic, Field & Francis LLP

(57) ABSTRACT

Methods of determining whether a sample includes one or more analytes, particularly proteinaceous analytes, of interest are provided. In the subject methods, an array of binding agents, where each binding agent includes an epitope binding domain of an antibody, is contacted with the sample. In many embodiments, contact occurs in the presence of a metal ion chelating polysaccharide, e.g., a pectin. Following contact, the presence of binding complexes on the array surface are detected and the resultant data is employed to determine whether the sample includes the one or more analytes of interest. Also provided are kits, systems and other compositions of matter for practicing the subject methods. The subject methods and compositions find use in a variety of applications, including proteomic applications such as protein expression analysis, e.g., differential protein expression profiling.

18 Claims, 23 Drawing Sheets

FOREIGN PATENT DOCUMENTS

| | | |
|---|---|---|
| WO | WO 99/35289 | 7/1999 |
| WO | WO 99/39210 | 8/1999 |
| WO | WO 99/40434 | 8/1999 |
| WO | WO 00/04382 | 1/2000 |
| WO | WO 00/04389 | 1/2000 |
| WO | WO 00/04390 | 1/2000 |
| WO | WO 00/54046 | 9/2000 |
| WO | WO 00/63701 | 10/2000 |
| WO | WO 01/14425 | 3/2001 |
| WO | WO 01/40803 | 6/2001 |

OTHER PUBLICATIONS

Elkins et al., Microarrays: Their Origins and Applications, Tibteck (Jun. 1999) 17:217-18.

Service, Protein Arrays Step Out of DNA's Shadow, Science (Sep. 11, 2000) 5485:1673.

* cited by examiner

|   D   |   C   |   B   |   A   |     |
|-------|-------|-------|-------|-----|
|   1   |  1:5  |   2   |  2:5  |  1  |
|   3   |  3:5  |   4   |  4:5  |  2  |
|   5   |  5:5  |   5   |  6:5  |  3  |
|  7d   |  7n   |  8d   |  8n   |  4  |
|   9   |  9:5  |  10d  |  10n  |  5  |
|  11   |  11:5 |  12   |  12:5 |  6  |
|  13   |  13:5 |  14d  |  14n  |  7  |
|  15d  |  15n  |  16   |  16:5 |  8  |
|  17d  |  17n  |  18d  |  18n  |  9  |
|  19d  |  19n  |  20d  |  20n  | 10  |
|  21   |  21:5 |  22   |  22:5 | 11  |
|  23d  |  23n  |  24   |  24:5 | 12  |

FIG. 5

Contribution of filtration of Cy3 labeled Ag mixture on background and signal intensity 3D-Link slide DVS slide Cy3　　　　　　　　Cy5
Prelabeled antigen mixes

HIGHLY SENSITIVE PROTEOMIC ANALYSIS METHODS, AND KITS AND SYSTEMS FOR PRACTICING THE SAME

CROSS-REFERENCE TO RELATED APPLICATIONS

Pursuant to 35 U.S.C. §119(e), this application claims priority to the filing date of U.S. Provisional Patent Application Ser. No. 60/234,527 filed Sep. 22, 2000, the disclosure of which is herein incorporated by reference.

INTRODUCTION

1. Field of the Invention

The field of this invention is proteomics.

2. Background of the Invention

Proteomics involves the qualitative and quantitative measurement of gene products and their activity by detecting and quantitating expression at the protein level, rather than at the messenger RNA level. Proteomics also involves the study of non-genome encoded events, including the post-translational modification of proteins, interactions between proteins, and the location of proteins within a cell. The structure, function, or level of activity of the proteins expressed by the cell are also of interest.

Essentially, proteomics involves the study of part or all of the status of the total protein contained within or secreted by a cell. Proteomics is of increasing interest for a number of reasons, including the fact that measuring the mRNA abundances of a cell potentially provides only an indirect and incomplete assessment of the protein content of the cell, as the level of active protein that is produced in a cell is often determined by factors other than the amount of mRNA produced, e.g. post-translational modifications, etc.

In many proteomic technologies being developed, an array of binding members, e.g., proteins, is employed to assay a sample for a multitude of protein analytes at the same time, in a manner analogous to that employed in array based genomics protocols. While a number of different protein array formats have been developed for use in proteomics and related applications, the formats developed to date are not without problems. Problems experienced with currently available formats include production issues resulting from potential inactivation of the protein upon attachment to the support surface, storage stability, changes in binding activity of the protein resulting from attachment to the support surface, performing the binding reaction at a solid/liquid interface, sensitivity issues, etc.

As such, there is continued interest in the development of new array formats and protocols that preferably overcome one or more of the above disadvantages often experienced with currently available formats.

Relevant Literature

U.S. patents of interest include: U.S. Pat. Nos. 4,514,508; 4,537,861; 4,591,570; 4,829,010; 5,100,777; 5,143,854; 5,171,695; 5,432,099; 5,436,170; 5,445,934; 5,486,452; 5,516,635; 5,532,128; 5,556,752; 5,599,720; 5,700,637; 5,763,175; 5,807,522; 5,863,722; 5,994,076; and 6,197,599. Also of interest are: WO 88/01058; WO 89/01157; WO 97/24455; WO 98/53103; WO 99/31267; WO 99/35289; WO 99/39210; WO 99/40434; WO 00/04382; WO 00/04389; WO 00/04390; WO 00/54046; WO 00/63701; WO 01/14425; and WO 01/40803. See also Service, Science (Sep. 8, 2000) 289: 1673.

SUMMARY OF THE INVENTION

Methods of determining, including quantitatively determining, whether a sample includes one or more analytes, particularly proteinaceous analytes, of interest are provided. In the subject methods, an array of binding agents, where each binding agent includes an epitope binding domain of an antibody, is contacted with the sample. In many embodiments, contact occurs in the presence of a metal ion chelating polysaccharide, e.g., a pectin. Following contact, the presence of binding complexes on the array surface are detected and the resultant data is employed to determine whether the sample includes the one or more analytes of interest. Also provided are kits and systems for practicing the subject methods. The subject methods and compositions find use in a variety of applications, including proteomic applications such as protein expression analysis, e.g., differential protein expression profiling.

BRIEF DESCRIPTION OF THE FIGURES

FIG. 5 provides a legend of an array of antibodies according to the subject invention.

DESCRIPTION OF THE SPECIFIC EMBODIMENTS

Figure 1:
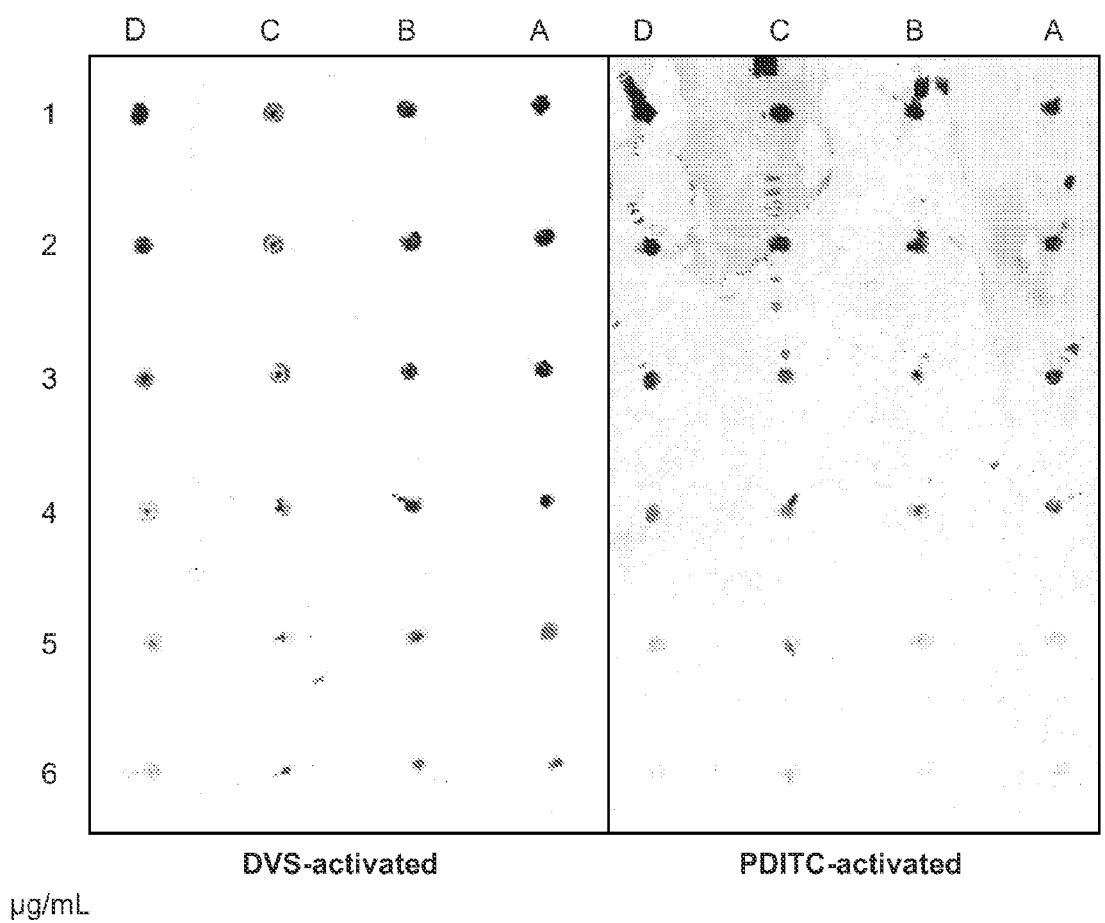
FIG. 1 is a computer generated image showing the results obtained with array manufactured from a DVS activated slide and PIDTC activated slide.

Methods of determining whether a sample includes one or more analytes, particularly proteinaceous analytes, of interest are provided. In the subject methods, an array of binding agents, where each binding agent includes an epitope binding domain of an antibody or another affinity capture ligand, is contacted with the sample. In many embodiments, contact occurs in the presence of a metal ion chelating polysaccharide, e.g., a pectin. Following contact, the presence of binding complexes on the array surface are detected and the resultant data is employed to determine whether the sample includes the one or more analytes of interest. Also provided are kits, systems and other compositions of matter for practicing the subject methods. The subject methods and compositions find use in a variety of applications, including proteomic applications such as protein expression analysis, e.g., differential protein expression profiling.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims. In addition, many modifications may be made to adapt a particular situation, material, composition of matter, process, process step or steps, to the objective, spirit and scope of the present invention. All such modifications are intended to be within the scope of the claims made herein.

In this specification and the appended claims, the singular forms "a," "an" and "the" include plural reference unless the context clearly dictates otherwise. Conversely, it is contemplated that the claims may be so-drafted to exclude any optional element. This statement is intended to serve as antecedent basis for use of such exclusive terminology as "solely," "only" and the like in connection with the recitation of claim elements or by use of a "negative" limitation.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Also, it is contemplated that any optional feature of the inventive variations described herein may be set forth and claimed independently, or in combination with any one or more of the features described herein.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All existing subject matter mentioned herein (e.g., publications, patents, patent applications and hardware) is incorporated by reference herein in its entirety. The referenced items are provided solely for their disclosure prior to the filing date of the present application. Nothing herein is to be construed as an admission that the present invention is not entitled to antedate such material by virtue of prior invention.

In further describing the subject invention, the methods are described first in greater detail, followed by a review of the kits and systems that find use in practicing the subject methods, as well as representative specific applications in which the subject methods find use.

Methods

General Features

As summarized above, the subject invention provides highly sensitive methods of determining the presence, often in at least semi-quantitative if not quantitative terms, of one or more, usually a plurality of, analytes in a sample. As the subject methods are highly sensitive, they are capable of detecting the presence of an analyte in a sample where the analyte is present in a low concentration. In many embodiments, the methods are capable of detecting an analyte in a sample where the analyte is present in a concentration as low as about 10 pg/mL or lower, where the concentration of the analyte may be as low as about 10 pg/mL, often as low as about 200 pg/mL or lower. As such, the lower limit of detection of the subject methods, i.e., the lowest analyte concentration detectable by the subject methods is in certain embodiments at least about 10 pg/mL, usually at least about 100 pg/mL and more usually at least about 200 pg/mL. In many embodiments, the methods are methods of detecting an analyte in a sample where the analyte concentration ranges from about 50 pg/mL to about 300 ng/mL, usually from about 100 pg/mL to about 100 ng/mL and more usually from about 200 pg/mL to about 30 ng/mL.

The subject methods are particularly suited for the detection of proteinaceous analytes, i.e., polypeptides, where the term polyeptide is used broadly to describe any molecule having two or more amino acid residues covalently bonded to each other by a peptide bond. As such, the subject methods are suitable for use in detecting analytes that are small polypeptides as well as whole proteins and fragments thereof. In many embodiments, the analytes are proteins.

In many embodiments, the subject methods are methods of simultaneously detecting, e.g., quantitatively, the presence of a plurality of analytes in a sample, where by "plurality" is meant two or more, usually about 5 or more and more usually about 10 or more, where in many embodiments at least about 20 different analytes, often at least about 50 and sometimes at least about 100 or more different analytes are assayed simultaneously.

Specific analytes of interest include, but are not limited to those listed in the following Antibody Table:

| Antibody Table | | | |
|---|---|---|---|
| 14-3-3 e v.2 | 53BP2 v.2 | ABP-280 | ABR |
| ACH ESTERASE | ACH rec B | ACTR/AIB1/RAC3 | adaptin alpha |
| adaptin beta | ADAPTIN d v.3 | Adaptin gamma | AF6/p180 |
| AFAP | AIM-1 | AKAP 149 | AKAP 79 |
| AKAP-KL | ALDH | alpha-/beta-SNAP | AMPHIPHYSIN |
| AMPK b v.2 | Annexin II | Annexin XI | AP 180 v.2 |

-continued

Antibody Table

| | | | |
|---|---|---|---|
| ApoE | APOLIPOPROTEIN B100 | App-BP1 | ARF-3 |
| ARGINASE I | ATAXIN-2 v.2 | ATTRACTIN | B CATENIN |
| B NAP v.2 | B56-alpha | BAG-1/RAP46 | BCL-2 |
| Bcl-xl | beta 1 Ca channel v.2 | beta-Arrestin1 | BM28 |
| BMX v.2 | Bog | bPIX | BRAMP2/AMPHIPHYSIN 2 |
| BRM | BRUCE | Btf | c-cbl |
| C-NAP1 | Cadherin (5) | Cadherin (E) | Cadherin (P) |
| CAF1 p150 | CALCINEURIN | Calnexin | CALRETININ v.2 |
| Calsequestrin | CAM KIN KIN v.2 | Casein K1e | casein kin.IIb |
| Casein kinase 1 epsilon | Catenin (alpha) | Cathepsin D | Cathepsin L |
| Caveolin 2 | CDC 34 | CDC 37 | CDC27 hs |
| CDC42GAP(Rac1) | CDK 2 | CDK4 | CDK7 |
| cGB-PDE v.2 | CHD3 | CHGB | Chromogranin A/CGA |
| CIP1 | CLA-1 | Clathrin HC | CLIP-115 |
| COL7A1 | COMT | Contactin v.2 | COX-2 |
| CPG16/DCAMKL1 v.3 | CRIK | CRP-1 | Csk |
| CUL-2 v.2 | CUL-3 | CYCLIN D3 | Cypher1 |
| DAP3 | DARPP-32 v.2 | DBP2 | DBP2 |
| DDX-1 | DEK | DEMATIN v.2 | DFF45 |
| DGK THETA v.2 | DHFR | DLG-1 v.2 | DLP1 |
| DMPK | DNA Polymerase delta | DNA Polymerase e (catalytic) | Doublecortin v.2 |
| DSIF | DYNAMIN 1 v.2 | Dynamin II | DYRK |
| EB1 | EBP50 v.2 | EEA-1 | eEF-2 kinase |
| Efp | Eg5 | EGF Recept | EGF Recept (activated) |
| EIF-4 gamma | eIF-4E | eIF-5A | Endoglin |
| Endothelin 1 Recept. | EphA4/ELF-1 | EPS-8 | ERG2 |
| ERp72 v.2 | ESE1 v.3 | Exportin-1/CRM1 | EXPORTIN-t v.3 |
| Ezrin | FADD v.2 | Fas | Fas Ligand |
| FBP v.2 | FEN-1 | FIN13 | FKBP 12 |
| FKBP51 | FKBP65 | FLAP v.2 | Flotilin-2/ESA |
| FNK v.2 | Frabin | FXR2 v.2 | FYB v.2 |
| G3BP | GABAbR2 v.2 | GAGE | GAP 1m |
| Gelsolin | Gephyrin | GLUCOCORTICOID | GM-CSF |
| GOK | GPI-phoslipase D. v.2 | GRIP | GS-15 |
| GSK 3B | GSPT2 | GST pi | Guanylate Kinase |
| HAP1 v.2 | HAX-1 | hcKROX | HDAC3 |
| HDJ-2 | HEME OXYGENASE 1 | HHR23B | HIC-5 v.2 |
| HIF-1a | HIF1b/ARNT1 | hILP (H59520) | hILP (H62120) |
| hPRP16 v.2 | hPRP17 | HRAD9 | HS-1 |
| Hsp-90 | Hsp10 | Hsp110 | HSP70 v.2 |
| IFN-¥ Human | IFN-¥ Rat | IKKb | IKKg/NEMO |
| IL-10 | IL-12 p40 | IL-12 p70 | IL-13 |
| IL-1β | IL-2 | IL-2 sRd | IL-3 |
| IL-4 | IL-5 | IL-6 | IL-8 |
| INHIBITOR 2 | iNOS/MAC NOS | Integrin æ5 | IP3 rec |
| IQGAP | IRS-1 v.6 | ISGF3 p48 | ITCH |
| JNKK1/MKK4 | K CHANNEL a SUB. | Kalinin B1 | Karyopherin B |
| KATANIN p80 | Ki-67 | KIF3B v.2 | KRIP-1 |
| KSR-1 v.3 | Ku70 | L-Caldesmon | LA PROTEIN |
| LAIR-1 v.2 | Lamp1/CD107a | LAR-PTP | LAT v.2 |
| LCK | LFA-1 alpha | LSP1 | LXRa v.3 |
| M33 | MAP4 | MCC | MCM5 |
| MCP-1 | MDC9 | Mek5 | Melusin |
| MENA | MINT1 v.2 | MINT3/XII gamma | MITOSIN |
| MKK7 v.2 | MONA | MRE II | MSH3 |
| MSH6/GTBP | MST-1 | MST-3 | MUPP1 v.2 |
| MXI-1 | MYR6 | NABC1/AIBC1 | NASP v.2 |
| NEDD-4 | Nek 2 | Nek3 | NES-1 |
| NESTIN | Neurexin I | NEUROGENIN 3 | NEUROGLYCAN v.2 |
| NEUROPILIN-2 | NEXILIN | NF kappa beta v.2 | NHE-1 |
| NHE-3 | Nhe-3 v.3 | NIP1 | NM23 |
| NMDAR2B v.2 | nNOS/NOS Type1 | NTF2 | NUCLEPORIN P62 v.2 |
| NuMA | Nup88 | p116 RIP v.2 | p19 SKP1 |
| p190-B v.3 | p36 | p38 delta v.2 | p47 PHOX |
| p52/LEDGF | P53 | p54nrb | p56 dok2 |
| P62DOK | PARP | Paxillin | PCMT-II |
| PCNA | PDGF Rec | PDI | PECI |
| PER2 | Pericentrin | Pex1 v.2 | PEX19 |
| PhLP | PI3-KINASE p110a v.6 | PI4-Kinase Beta | PIN |

-continued

Antibody Table

| | | | |
|---|---|---|---|
| PIP5Kg | PKC EPSILON | PKC iota | PKC LAMBDA* |
| PKC THETA | PKR v.3 | PLAKOPHILIN 2a | PLC beta 1 v.2 |
| PLC delta 1 | PLK | PMF-1 | PNUTS |
| PRK2 v.2 | R cadherin v.2 | RAB 27 | RAB-5 |
| RAB11 | RAB4 | Rabphilin 3A | RACK 1 |
| RAP 2 | RAS (Ha) | RAS-GRF2 v.2 | RB2 |
| RCH-1 | REF-1 | RNAse H1 | ROAZ v.2 |
| ROK alpha | sCD23 | SCP3 | SH2-B v.2 |
| Shc C | SII | SIII p15 | SIP1 |
| SKAPP55 v.2 | SLP76 | SMAD2 v.2 | SMAD4 |
| SMN v.2 | SNX1 v.3 | SNX2 | SPA-1 v.2 |
| SPOT I4 | SQS | SRP54 | SRPK1 |
| SSeckS | STAT-3 | STAT6/IL-4 STAT v.5 | STI1 |
| SYNAPTOGYRIN | Synaptophysin | Synaptotagmin | Syntaxin 4 |
| SYNTAXIN 6 v.2 | TAF 70-alpha | TAF-172 | Tat-SF1 |
| TENSIN | TFII-1 | TGF-β | THROMBOSPONDIN 1 |
| TIAR | TIEG2 | TLS | TNF-œ |
| TOPO IIa v.2 | TOPO IIb | TPL-2 | TRADD v.2 |
| TRAX | TREX 1 | TRF2 | TRP1 |
| UBE3A | V-1/myotrophin | VASP | Veli1 |
| VESL-1L | VHR | VLA-3 alpha SUBUNIT | VTI1b |
| WRN | XIN | XPD | ZAP-70K |
| ZBP-89 | ZFP-37 | ZO-1 | |

Of particular interest in certain embodiments are assays in which at least about 5 of the above analytes are assayed, often at least about 10, at least about 20, at least about 25, at least about 50 and sometimes at least about 100, at least about 200, at least about 300, at least about 400 or more of the above specific analytes are assayed.

The subject methods may be used with a variety of different types of samples and still provide the above described sensitivity. As such, the sample may be a highly complex sample, such as a crude cell extract, or an at least partially purified sample, as desired. Because of the convenience, in many embodiments the sample is a crude cell extract, where the only treatment employed may be a dilution step and/or removal of cellar debris step. A more in depth description of different types of samples with which the subject methods may be employed is provided below.

Arrays

A feature of the subject methods is the use of an array of a plurality of distinct binding agents, wherein each binding agent includes at least an epitope binding domain of an antibody molecule. The arrays employed in the subject methods are characterized by having a plurality of probe spots, each made up of a distinct binding agent (i.e., a plurality of copies of distinct binding agent molecule) stably associated with the surface of a solid support.

Each probe composition of the subject arrays is made up of multiple copies of a binding agent, where each binding agent includes at least an epitope binding domain of antibody. By epitope binding domain is meant a region or portion of an antibody molecule that specifically binds to an antigen, more particularly a determinant or epitope of a given antigen. As such, of particular interest as binding agents are antibodies, as well as specific antigen binding fragments and mimetics thereof. Where antibodies are the binding agent, they may be derived from polyclonal compositions, such that a heterogeneous population of antibodies differing by specificity are each immobilized on the substrate surface, or monoclonal compositions, in which a homogeneous population of identical antibodies that have the same specificity for the target analyte, e.g., protein, are each immobilized on the substrate surface. As such, the binding agent may be either a monoclonal or a polyclonal antibody in certain embodiments.

In yet other embodiments, the binding agent making up the subject probe compositions is an antibody binding fragment or mimetic, where these fragments and mimetics have the requisite binding affinity for the target analyte, e.g., protein. For example, antibody fragments, such as Fv, F(ab)$_2$ and Fab may be prepared by cleavage of the intact protein, e.g. by protease or chemical cleavage. Also of interest are recombinantly produced antibody fragments, such as single chain antibodies or scFvs, where such recombinantly produced antibody fragments retain the binding characteristics of the above antibodies, i.e., they include the epitope binding domain (which means the whole domain or a least a functional portion thereof) of an antibody specific for the particular analyte. Such recombinantly produced antibody fragments generally include at least the $V_H$ and $V_L$ domains of the subject antibodies, so as to retain the binding characteristics of the subject antibodies. These recombinantly produced antibody fragments or mimetics of the subject invention may be readily prepared using any convenient methodology, such as the methodology disclosed in U.S. Pat. Nos. 5,851,829 and 5,965,371; the disclosures of which are herein incorporated by reference. The above described antibodies, fragments and mimetics thereof may be obtained from commercial sources and/or prepared using any convenient technology, where methods of producing polyclonal antibodies, monoclonal antibodies, fragments and mimetics thereof, including recombinant derivatives thereof, are known to those of the skill in the art. The binding agents typically have a strong affinity for their analyte, where this affinity is at least about $10^{-6}$, usually at least about $10^{-8}$ and typically ranges from about $10^{-8}$ to about $10^{-13}$, usually from about $10^{-9}$ to about $10^{-12}$, where the affinity is the affinity as measured following immobilization of the antibody onto the surface using the binding affinity assay described in Pellequer, J. L., Van Regenmortel, M. H., J Endocrinol, 139, (3) 495-501.

The probe spots made up of the binding agents as described above and present on the array may be any convenient shape, but will typically be circular, elliptoid, oval or some other analogously curved shape. The total amount or mass of molecules present in each spot will be sufficient to provide for adequate hybridization and detection of analytes during the assay in which the array is employed. Generally, the total mass of binding agents in each spot will be at least about 10 pg, usually at least about 100 pg and more usually at least about 1 ng, where the total mass may be as high as 20 ng or higher, but will usually not exceed about 10 ng and more usually will not exceed about 5 ng. The copy number of all of the individual binding agents in a spot will be sufficient to provide enough hybridization sites for tagged target molecule to yield a detectable signal, and will generally range from about 100 FU to about 65500 FU, usually from about 250 FU to about 45000 FU.

Where the probe spot has an overall circular dimension, the diameter of the spot generally ranges from about 10 to about 5,000 μm, usually from about 20 to about 1,000 μm and more usually from about 50 to about 500 μm. The surface area of each spot is at least about 100 $\mu m^2$, usually at least about 200 $\mu m^2$ and more usually at least about 400 $\mu m^2$, and may be as great as about 25 $mm^2$ or greater, but will generally not exceed about 5 $\mu m^2$, and usually will not exceed about 1 $mm^2$. The density of binding agents "probe" spots on the array, as well as the overall density of probe and non-probe spots (where the latter are described in greater detail below) may vary greatly. As used herein, the term spot refers to any spot on the array surface that is made up of binding agents, whether control or probe binding agents, and as such includes both probe spots and non-probe spots. The density of the probe spots on the solid surface is at least about 5/$cm^2$ and usually at least about 10/$cm^2$ and may be as high as about 100/$cm^2$, about 200/$cm^2$, about 300/$cm^2$, about 500/$cm^2$, about 1000/$cm^2$, about 5000/$cm^2$ or higher, but in many embodiments does not exceed about 1000/$cm^2$, and in these embodiments usually does not exceed about 500/$cm^2$ or about 400/$cm^2$ in many embodiments, and in certain embodiments does not exceed about 300/$cm^2$. The spots may be arranged in a spatially defined and physically addressable manner, in any convenient pattern across or over the surface of the array, such as in rows and columns so as to form a grid, in a circular pattern, and the like, where generally the pattern of spots will be present in the form of a grid across the surface of the solid support.

In the subject arrays, the spots of the pattern are stably associated with or immobilized on the surface of a solid support, where the support may be a flexible or rigid support. By "stably associated" it is meant that the binding agents of the spots maintain their position relative to the solid support under incubation and washing conditions, as described below and explicitly exemplified in the Experimental Section below. As such, the individual binding agent members that make up the spots can be non-covalently or covalently stably associated with the support surface based on technologies well known to those of skill in the art. Examples of non-covalent association include non-specific adsorption, binding based on electrostatic (e.g. ion, ion pair interactions), hydrophobic interactions, hydrogen bonding interactions, specific binding through a specific binding pair member covalently attached to the support surface, and the like. Examples of covalent binding include covalent bonds formed between the spot binding agents and a functional group present on the surface of the rigid support, where the functional group may be naturally occurring or present as a member of an introduced linking group. In many preferred embodiments, the binding agents making up the spots on the array surface, are covalently bound to the support surface, e.g., through covalent linkages formed between moieties present on the binding agents, e.g., amines, and the substrate surface, etc, as may be present on a glass substrate, e.g., aminated glass. See e.g., the specific covalent attachment protocol exemplified below.

As mentioned above, the array is present on either a flexible or rigid substrate. By flexible is meant that the support is capable of being bent, folded or similarly manipulated without breakage. Examples of solid materials which are flexible solid supports with respect to the present invention include membranes, flexible plastic films, and the like. By rigid is meant that the support is solid and does not readily bend, i.e. the support is not flexible. As such, the rigid substrates of the subject arrays are sufficient to provide physical support and structure to the polymeric targets present thereon under the assay conditions in which the array is employed, particularly under high throughput handling conditions. Furthermore, when the rigid supports of the subject invention are bent, they are prone to breakage.

The solid supports upon which the subject patterns of spots are presented in the subject arrays may take a variety of configurations ranging from simple to complex, depending on the intended use of the array. Thus, the substrate could have an overall slide or plate configuration, such as a rectangular or disc configuration. In many embodiments, the substrate will have a rectangular cross-sectional shape, having a length of from about 10 mm to 200 mm, usually from about 40 to 150 mm and more usually from about 75 to 125 mm and a width of from about 10 mm to 200 mm, usually from about 20 mm to 120 mm and more usually from about 25 to 80 mm, and a thickness of from about 0.01 mm to 5.0 mm, usually from about 0.01 mm to 2 mm and more usually from about 0.01 to 1 mm. Thus, in one representative embodiment the support may have a micro-titre plate format, having dimensions of approximately 125×85 mm. In another representative embodiment, the support may be a standard microscope slide with dimensions of from about 25×75 mm.

The substrates of the subject arrays may be fabricated from a variety of materials. The materials from which the substrate is fabricated should ideally exhibit a low level of non-specific binding during binding events. In many situations, it will also be preferable to employ a material that is transparent to visible and/or UV light. For flexible substrates, materials of interest include: nylon, both modified and unmodified, nitrocellulose, polypropylene, and the like. For rigid substrates, specific materials of interest include: glass; plastics, e.g. polytetrafluoroethylene, polypropylene, polystyrene, polycarbonate, and blends thereof, and the like; metals, e.g. gold, platinum, and the like; etc. Also of interest are composite materials, such as glass or plastic coated with a membrane, e.g., nylon or nitrocellulose, etc.

The substrates of the subject arrays comprise at least one surface on which the pattern of spots is present, where the surface may be smooth or substantially planar, or have irregularities, such as depressions or elevations. The surface on which the pattern of spots is present may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like. Polymeric layers of interest include layers of: peptides, proteins, polynucleic acids or mimetics thereof, e.g. peptide nucleic acids and the like; polysaccharides, phospholipids, polyurethanes, polyesters, polycarbonates, polyureas, polyamides, polyethyleneamines, polyarylene sulfides, polysiloxanes, polyimides, polyacetates, polyacrylamides, and the like, where the polymers may be hetero- or homopolymeric, and may or may not have separate functional moieties attached thereto, e.g. conjugated.

In certain embodiments, e.g., where the binding agent is a whole antibody or analogous structure, an antibody universal binding layer is present on the substrate surface, e.g., covalently bound to the substrate surface, which layer acts as a linking group or tethering element between the antibody binding agent in the substrate surface and serves to tether the antibody binding agent to the substrate surface. The basic principle is to utilize proteins and ligands with affinity towards antibodies (including but not limited to Protein A, Protein G, Protein L, Protein LA) which are covalently immobilized to a glass, plastic or any other type of surfaces. After the immobilization of the universal binding layer, the antibody binding agents are deposited on the same locations and reversibly immobilized. The universal binding layer of affinity ligands thus forms a layer which protects the consequently bound antibodies from detrimental surface effects. An additional benefit is the directed mode of immobilization as compared to that of direct covalent attachment of the antibodies to activated surfaces. This results in 100% availability of the antigen binding sites on the antibodies for consequent detection of antigens. It also provides universal conditions for binding, since the formation of ligand/antibody complex is obtained under mild physiological conditions where as covalent immobilization of proteins is often performed under conditions that might be detrimental to their biological activity.

The total number of spots on the substrate will vary depending on the number of different probe spots (binding agent probe compositions) one wishes to display on the surface, as well as the number of non probe spots, e.g., control spots, orientation spots, calibrating spots and the like, as may be desired depending on the particular application in which the subject arrays are to be employed. Generally, the pattern present on the surface of the array will comprise at least about 10 distinct spots, usually at least about 20 spots, and more usually at least about 50 distinct spots, where the number of distinct spots may be as high as 10,000 or higher, but will usually not exceed about 5,000 distinct spots, and more usually will not exceed about 3,000 distinct spots and in many instances will not exceed about 2,000 distinct spots. In certain embodiments, it is preferable to have each distinct probe spot or probe composition be presented in duplicate, i.e. so that there are two duplicate probe spots displayed on the array for a given target. The number of probe spots present in the array will typically make up a substantial proportion of the total number of spots on the array, where in many embodiments the number of probe spots is at least about 50 number %, usually at least about 80 number % and more usually at least about 90 number % of the total number of spots on the array. As such, in many embodiments the total number of spots on the array ranges from about 10 to about 20,000, usually from about 20 to about 10,000 and more usually from about 100 to 5,000.

In the arrays of the subject invention (particularly those designed for use in high throughput applications, such as high throughput analysis applications), a single pattern of probe spots may be present on the array or the array may comprise a plurality of different spot patterns, each pattern being as defined above. When a plurality of different spot patterns are present, the patterns may be identical to each other, such that the array comprises two or more identical spot patterns on its surface, or the spot patterns may be different, e.g. in arrays that have two or more different sets of probes present on their surface, e.g., an array that has a pattern of spots corresponding to first population of target analytes and a second pattern of spots corresponding to a second population of analytes. Where a plurality of spot patterns are present on the array, the number of different spot patterns is at least 2, usually at least 6, more usually at least 24 or 96, where the number of different patterns will generally not exceed about 384.

Where the array includes a plurality of spot patterns on its surface, preferably the array includes a plurality of reaction chambers, wherein each chamber has a bottom surface having associated therewith an pattern of spots and at least one wall, usually a plurality of walls surrounding the bottom surface. See e.g. U.S. Pat. No. 5,545,531, the disclosure of which is herein incorporated by reference. Of particular interest in many embodiments are arrays in which the same pattern of spots in reproduced in 24 or 96 different reaction chambers across the surface of the array.

Within any given pattern of spots on the array, there may be a single spot that corresponds to (i.e., specifically binds to) a given analyte target or a number of different spots that correspond to the same analyte, where when a plurality of different spots are present that correspond to the same analyte, the probe compositions of each spot that corresponds to the same analyte may be identical or different. In other words, a plurality of different analytes are represented in the pattern of spots, where each analyte may correspond to a single spot or a plurality of spots, where the probe compositions among the plurality of spots corresponding to the same analyte may be the same or different. Where a plurality of spots (of the same or different composition) corresponding to the same analyte is present on the array, the number of spots in this plurality will be at least about 2 and may be as high as 10, but will usually not exceed about 5. As mentioned above, however, in many preferred embodiments, any given analyte is represented by only a single type of probe spot, which may be present only once or multiple times on the array surface, e.g. in duplicate, triplicate etc.

The number of distinct or different probe spots present on the array, and therefore the number of different analytes represented on the array, is at least about 2, usually at least about 10 and more usually at least about 20, where in many embodiments the number of different analytes represented on the array is at least about 50 and more usually at least about 100. The number of different analytes represented on the array may be as high as 5,000 or higher, but in many embodiments will usually not exceed about 3,000 and more usually will not exceed about 2,500. An analyte is considered to be represented on an array if it is able to specifically bind to one or probe compositions on the array.

The arrays employed in the subject methods may be fabricated using any convenient protocol, where the protocol may vary depending on the nature of the substrate, the nature of any intervening surface layer, e.g., whether or not a universal binding layer is present, and the nature of the binding agents. Where the substrate is a glass substrate or analogous material, typically the surface of the substrate is first activated to provide for functional groups suitable for use in the covalent bonding, either directly or through a linking group, of the binding agent. For example, glass surfaces may be aminated so as to display amine functional groups via silanization, according to well known surface chemistry protocols. In many embodiments, the binding agent is then immobilized on the functionalized surface, e.g., through direct or indirect covalent bonding, e.g., by non-covalent binding to a covalently bound universal binding layer of molecules, as described above. Of particular interest in many embodiments is the use of a surface activation agent, e.g., that provides a linking group capable of forming a covalent linkage between aminated moieties, such as PIDTC and DVS, as exemplified in the experimental section below.

Following surface preparation, e.g., surface activation, a binding agent composition is immobilized on the substrate surface to produce a spot of the array. The binding agent composition is typically an aqueous composition. Preferably, the concentration ranges of the deposited binding agent composition is at least about 0.1 mg/mL, usually at least about 0.2 mg/mL, where the concentration may be as great as 1 mg/mL or greater. The purity of the binding agent composition typically is at least about 90%, usually at least about 95% and more usually at least about 97% % pure.

The binding agent composition is deposited on the array surface using any convenient protocol. In many embodiments, the binding agent composition is applied using a pin or analogous deposition device. Also of interest are pipette devices, ink jet devices, etc., which are extensively described in the array preparation art. The particular device and protocol employed to spot the subject binding agents is not critical, so long as it results in a functional probe spot, i.e., a probe spot that specifically binds to its target analyte.

Following deposition of the binding agent compositions to produce the pattern of probe spots on the array, the surface is then contacted with a blocking agent in order to block non-specific binding sites on the array surface. Any convenient blocking agent may be employed, where representative blocking agents include, but are not limited to, nonfat milk, BSA, gelatin, preimmune serum and the like, where standard blocking protocols may be employed.

Following preparation and blocking, as described above, the array is typically stored for a period of time prior to use. The array may be stored in any convenient format, including both dry and wet formats, so long as the activity of the array, i.e., the binding ability of the probe spots on the array for their specific analytes, is not adversely affected. By not adversely affected is meant that the sensitivity of the array does not change with respect to a given analyte as compared to the array immediately following blocking by a value that exceeds about 10 fold, and usually does not change by a value that exceeds about 5 fold. In many embodiments, the period of time for which the array is stored prior to use in the subject methods, described in greater detail below, is at least about 2 days, usually at least about 6 months and more usually at least about 9 months and may be as long as about 1 year or longer, where the array is typically not stored for a period that exceeds about 6 months prior to use, Sample The sample that is contacted with the substrate surface may vary greatly, depending upon the nature of the assay to be performed. In general, the sample is an aqueous fluid sample. The amount of fluid sample also varies with respect to the nature of the device, the nature of the sample, etc. In many embodiments, the amount of sample that is contacted with the substrate surface ranges from about 100 µl to about 10 ml, usually from about 1 mL to about 8 ml and more usually from about 4 to about 6 ml.

In many embodiments, the fluid sample is a naturally occurring sample, where the sample may or may not be modified prior to contact with the substrate. In many embodiments, the fluid sample is obtained from a physiological source, where the physiological source is typically eukaryotic, with physiological sources of interest including sources derived from single celled organisms such as yeast and multicellular organisms, including plants and animals, particularly mammals, where the physiological sources from multicellular organisms may be derived from particular organs or tissues of the multicellular organism, or from isolated cells or cellular compartments, e.g., nucleus, cytoplasm, etc., derived therefrom.

In obtaining the fluid sample, the initial physiological source (e.g., tissue, collection of cells, etc.) may be subjected to a number of different processing steps, where such processing steps might include tissue homogenation, nucleic acid extraction and the like, where such processing steps are known to the those of skill in the art. Of particular interest in many embodiments is the use of cellular extracts as the sample.

In certain embodiments, the initial fluid sample derived from a particular source, e.g., a cell extract, may be subjected to a fractionation protocol that reduces the complexity of the protein composition of the sample. By reduce the complexity is meant that the total mass of all of the proteins in the sample is reduced by at least about 10 fold, usually by at least about 100 fold and more usually at least about 1000 fold.

In certain embodiments, the fractionation protocol employed is one that reduces the amount of highly abundant proteins in the sample. In this embodiment, a pool of covalently attached antibodies, e.g., one or more columns of antibodies, is employed for enrichment of antigen analytes of interest from an initial sample, e.g., whole cell extracts. After reversible adsorption of the antigens of interest on the multi-antibody column, the non adsorbed material is washed away with washing buffer and the specifically retarded antigens are eluted and collected for further labeling and incubation with the array containing binding agent spots for the antigen/analytes of interest, e.g., the same antibodies that were used for initial enrichment. In this manner, the initial sample is fractionated so as to reduce the complexity and enrich the sample for the analytes of interest.

In many embodiments, though not necessarily all embodiments, the analytes of interest present in the sample are labeled prior to contact with the array, described in greater detail in the next section. By labeled is meant that the analytes are modified to be joined to, either covalently bonded to or stably but non-covalently bound to, a member of a signal producing system and are thus detectable, either directly or through combined action with one or more additional members of a signal producing system. Examples of directly detectable labels include isotopic and fluorescent moieties. Isotopic moieties or labels of interest include $^{32}P$, $^{33}P$, $^{35}S$, $^{125}I$, $^{3}H$, and the like. Fluorescent moieties or labels of interest include coumarin and its derivatives, e.g. 7-amino-4-methylcoumarin, aminocoumarin, bodipy dyes, such as Bodipy FL, cascade blue, fluorescein and its derivatives, e.g. fluorescein isothiocyanate, Oregon green, rhodamine dyes, e.g. texas red, tetramethylrhodamine, eosins and erythrosins, cyanine dyes, e.g. Cy3 and Cy5, macrocyclic chelates of lanthanide ions, e.g. quantum Dye™, fluorescent energy transfer dyes, such as thiazole orange-ethidium heterodimer, TOTAB, etc. Labels may also be members of a signal producing system that act in concert with one or more additional members of the same system to provide a detectable signal. Illustrative of such labels are members of a specific binding pair, such as ligands, e.g. biotin, fluorescein, digoxigenin, antigen, polyvalent cations, chelator groups and the like, where the members specifically bind to additional members of the signal producing system, where the additional members provide a detectable signal either directly or indirectly, e.g. antibody conjugated to a fluorescent moiety or an enzymatic moiety capable of converting a substrate to a chromogenic product, e.g. alkaline phosphatase conjugate antibody; and the like.

The analytes may be labeled according to any convenient protocol, where the particular protocol employed may vary greatly with respect to the overall assay protocol being practiced and the nature of the specific label. For example, where the analytes are labeled with detectably labeled antibodies, e.g., fluorescently labeled antibodies, the labeling protocol typically comprises contacting the analyte with the labeled antibodies and incubating the sample under conditions sufficient for the labeled antibody to specifically bind to the analyte in the sample. In these embodiments, the labeled antibodies employed as labeling reagents are specific for an epitope of the analyte that is available for binding even when the analyte is bound to a probe spot on the array surface.

In certain preferred embodiments, the analytes of interest are labeled with functionalized label reagent that covalently bond to the analytes. In this embodiments, the analyte containing fluid sample is contacted with functionalized label under conditions sufficient for a functional moiety of the analyte, e.g., an amine group, to react with the corresponding functional moiety present on the label to produce a covalent bond between the label and the analyte. As such, functionalized labels employed in these embodiments of the subject methods include a functional moiety and a label moiety.

The functional moiety of the functionalized labels may vary greatly, and is chosen in view of the functional moiety present on the analytes in the sample, e.g., amine groups on the proteins analytes present in the sample. In other words, the functional moiety present on the functionalized label must be one that reacts with the functional moiety present on the analyte to produce a covalent bond between the analyte and the label. Representative functional moieties that may be present on the label include: amino, sulfhydryl, sulfoxyl, aminosulfhydryl, azido, epoxide, isothiocyanate, isocyanate, anhydride, monochlorotriazine, dichlorotriazine, mono- or dihalogen substituted pyridine, mono- or disubstituted diazine, maleimide, epoxide, aziridine, sulfonyl halide, acid halide, alkyl halide, aryl halide, alkylsulfonate, N-hydroxysuccinimide ester, imido ester, hydrazine, azidonitrophenyl, azide, 3-(2-pyridyl dithio)-propionamide, glyoxal, aldehyde, iodoacetyl, cyanomethyl ester, p-nitrophenyl ester, o-nitrophenyl ester, hydroxypyridine ester, carbonyl imidazole, and the like.

Consistent with the general description of suitable labels above, the label component of the functionalized label may be directly or indirectly detectable, but is generally directly detectable. Examples of directly detectable labels include isotopic and fluorescent labels. Isotopic moieties or labels of interest include $^{32}P$, $^{33}P$, $^{35}S$, $^{125}I$, and the like. Fluorescent moieties or labels of interest include coumarin and its derivatives, e.g. 7-amino-4-methylcoumarin, aminocoumarin and hydroxycoumarin, BODIPY dyes, such as BODIPY FL, cascade blue, Cascade Yellow, fluorescein and its derivatives, e.g. fluorescein isothiocyanate, Oregon green, Marina Blue, rhodamine dyes, e.g. rhodamine red, tetramethylrhodamine and rhodamine 6G, Texas Red, eosins and erythrosins, cyanine dyes, e.g. Cy3 and Cy5, macrocyclic chelates of lanthanide ions, e.g. quantum dye, fluorescent energy transfer dyes, such as thiazole orange-ethidium heterodimer, TOTAB, Alexa, etc. Labels can also be proteins with luminescent properties, e.g. green fluorescent protein, phicoerythrin, etc. Also of interest are particle labels, e.g. light scattering particles. Labels may also be members of a signal producing system that act in concert with one or more additional members of the same system to provide a detectable signal. Illustrative of such labels are members of a non-covalent specific binding pair, such as ligands, e.g. biotin, fluorescein, digoxigenin, other haptens, polyvalent cations, chelator groups and the like, where the members specifically bind to additional members of the signal producing system, where the additional members provide a detectable signal either directly or indirectly, e.g. antibody conjugated to a fluorescent moiety or an enzymatic moiety capable of converting a substrate to a chromogenic or fluorescent product or a product that emits light, e.g. alkaline phosphatase conjugate antibody, luciferase, horseradish peroxidase; and the like. In many embodiments, however, the label is a fluorescent label which is modified to include a functional moiety, as described above.

In certain preferred embodiments where the analytes are labeled prior to contact with the array, the sample preparation protocol employs a single type of buffer for both the cellular extraction and labeling steps. In other words, a single buffer composition is employed in both the extraction step, where the proteins of the cell are separated from other cellular components/structures, and in the labeling step, where the analytes present in extract are labeled with a detectable label. The single extraction/labeling buffer employed in these embodiments is one that provides for high extraction efficiency, where high extraction efficiency is meant at least about 90% and usually at about 95% (by weight) of the proteins are extracted with the extraction/labeling buffer, as compared to the amount of proteins extracted by SDS boiling. In addition, the buffer is a buffer that is extracts proteins from all cellular compartments/locations. This single cellular extract/labeling buffer is typically characterized by including detergents and other components, when present, that are free of primary amines. Representative detergents employed that may be present in the buffer include, but are not limited to: octyl-β-D-glucopyranoside (ODG), NP-40, Empigen, Pluronic, and the like. The amount of each detergent present in the extraction/labeling buffer may vary, but typically ranges from about 0.01% to about 10%, usually from about 0.05% to about 5% and more usually from about 0.1% to about 2%. In addition, the pH of the buffer is selected such that it provides for suitable conditions for both cellular extraction and labeling. As such, the pH typically ranges from about 7 to about 12, usually from about 8 to about 10.

Where the same extraction and labeling buffer is employed, general extraction and labeling protocols are practiced, where representative protocols are provided below. Following labeling, it may be desirable to include a desalting step, as is described in the Experimental section below.

Incubation

Following sample preparation and any analyte labeling, where desired, the analyte containing fluid sample is contacted with the array of binding agents and contact is maintained under sufficient conditions and for a period of time sufficient for binding of analyte to specific binding pair members on the array surface to occur. Typically, the array and analyte containing sample are incubated together for at least about 10 min., usually at least about 20 min., and more usually at least about 30 min., where the incubation time may be as long as about 480 min. or longer, but typically does not exceed about 60 min. During incubation, the array and sample are maintained at a temperature that typically ranges from about 20° C. to about 28° C., usually from about 22° C. to about 26° C. In many embodiments, the array and sample are subjected to mixing or agitation during the incubation step.

A feature of the incubation step is that present in the analyte containing fluid medium contacted with the array surface during incubation is a metal ion chelating polysaccharide, i.e., a polysaccharide that chelates metal ions, wherein the polysaccharide is typically a charged molecule. The polysaccharide may be a naturally occurring or synthetic molecule, and may be a homopolymeric or heteropolymeric compound.

The molecular weight of the polysaccharide may vary greatly, but typically ranges from about 10,000 to 2,500,000 daltons, usually from about 10,000 to 500,000 daltons, where typically a population of polysaccharide molecules of different weights are present in the analyte containing fluid medium during incubation. The total amount of metal chelating polysaccharide present in the analyte containing fluid medium typically ranges from about 0.01% to about 2%, usually from about 0.2% to about 1%. In certain embodiments, the metal chelating polysaccharide is a heteropolymeric compound that includes polygalactouronate sequences. Of particular interest in certain embodiments are pectins, like fruit pectins, e.g., citrus pectin (e.g., lemon, orange), apple pectin, tomato pectin, and the like.

During incubation, the pH of the liquid medium is typically maintained at a value ranging from about 6.5 to about 8.5, usually from about 7.0 to about 8.0. Also present may be one or more buffers, e.g., Tris, sodium citrate and the like; salts, e.g., NaCl, sodium sulfate, and the like; surfactants/surfactants, e.g., Pluronics, Tweens, glycerol, ethylene glycol, etc.

While the contact of the array and analyte containing fluid medium, as well as metal chelating polysaccharide, may be accomplished using any convenient protocol, in many embodiments, the initial sample is first pre-incubated with an incubation buffer that includes the metal ion chelating polysaccharide to produce a preincubated analyte containing sample, which preincubated sample is then contacted with the array for the incubation period. In these embodiments, the incubation buffer employed at least includes the metal ion chelating polysaccharide as described above. In addition, the incubation buffer typically includes a number of additional components, including buffering agents, salts, surfactants, etc.

Washing

Following incubation, non-array bound components of the analyte containing medium contacted with the array surface during incubation are separated or removed from the surface. This separation step is typically accomplished using one or more washing steps, in which the array surface is contacted and separated from, including flushed with, one or more different fluid compositions.

In a preferred embodiment, the array surface is subjected to a sequential washing protocol, in which the array surface is washed with a plurality of distinct washing solutions. The number of different washings employed in these embodiments varies, but typically ranges from about 3 to 10, usually from about 5 to 9 and more usually from about 6 to 8, where in certain embodiments, 7 distinct washings are employed. See e.g., the representative washing protocol employed in the experimental section, below.

In these embodiments, the series of different washing mediums employed provides a modulation or change in the nature of the washing medium and components therein, e.g., in order to subject the array surface to a sequential or stepwise change or modulation of conditions, e.g., amount/type of detergent, salt concentration, buffering agent, additives, etc. In these embodiments, the different washing conditions to which the array is subjected during the sequential wash protocol are ones that provide for a decrease in background and cross-reactivity during detection, and therefore an increase in signal to noise ratio and/or selectivity, so as to provide the sensitive results discussed above. In certain embodiments, the washing conditions are ones that provide for an increase in signal to noise ratio and/or selectivity of at least about 2-fold, usually at least about 5 fold and more usually at least about 10 fold and compared to a control assay in which only a single wash step with a wash fluid that is the same as the incubation fluid is performed. In certain preferred embodiments, the sequential wash protocol is characterized by initially employing a high salt wash, e.g., to remove electrostatically bound molecules, followed by sequential use of wash fluids of decreasing detergent composition, and/or a change of buffers, e.g., from Tris to sodium citrate. Of particular interest in certain embodiments is the use of an fluorescence quenching decreasing agent, e.g., polyethyleneimine and other agents that provide for a decrease in fluorescence quenching and therefore an increase in signal to noise ratio.

Optional Labeling

If the analytes in the sample are not labeled prior to incubation, as described above, they are labeled at some point prior to detection, described below. As such, the surface bound analytes may be labeled following incubation and an initial wash step, e.g., where the labels are labeled antibodies capable of binding to already surface bound analytes. Alternatively, the labels may be functionalized to covalently bind to any molecule displaying a corresponding functional group, e.g., a primary amine. In these embodiments, the sample incubated array is contacted with the labeling composition under conditions sufficient for labeling to occur. An initial signal is then obtained from the array, followed by a washing step to remove bound analytes and other components. A second signal is then obtained. This second signal is then subtracted from the initial signal to obtain a final signal that is representative or related to the amount of analyte bound to the array, which signal is employed as described below to derive the amount of analyte in the sample. See the Experimental section below for further details.

Detection of Binding Complexes on the Array Surface

Following washing, the array surface is read or scanned for the presence of binding complexes between analytes in the assayed sample and binding agents of the probe spots of the array. In other words, analyte/binding agent complexes on the surface of the array are detected.

Any convenient protocol may be employed for detecting the binding agents on the array surface. Many different protocols for detecting the presence of surface bound binding complexes are known to those of skill in the art, where the detection method may be qualitative or quantitative depending on the particular application in which the subject method is being performed, where the particular detection protocol employed may or may not use a detectable label. Representative detection protocols that may be employed include those described in WO 00/04389 and WO 00/04382; the disclosures of the priority applications of which are herein incorporated by reference. Representative non-label protocols include surface plasmon resonance, total internal reflection, Brewster Angle microscopy, optical waveguide light mode spectroscopy, surface charge elements, ellipsitometry, etc., as described in U.S. Pat. No. 5,313,264, the disclosure of which is herein incorporated by reference. Alternatively, detectable label based protocols, including protocols that employ a signal producing system, may be employed. The particular protocol employed varies, depending on the nature of the label that is employed. Where fluorescent labels are employed, any convenient fluorescence scanner device, i.e., fluorimeter, may be employed, where numerous such devices and methods for their use are known to those of skill in the art.

Analyte Determination

Following detection of the surface bound binding complexes, the presence of any surface bound binding complexes is then related to the presence of the one or more analytes in the sample. In many embodiments, the signal intensity value obtained for any binding complex is quantitatively related to the presence of the corresponding analyte in the sample, so as to provide a quantitative determination of the analyte amount in the sample. This relating step is readily accomplished in that the position on the array at which a particular surface bound complex is located indicates the identity of the analyte or protein, since the binding agent for the protein is attached to a known specific location on the array. Thus, this relating step merely comprises determining the location on the array on which a binding complex is present, comparing that location to a reference that provides information regarding the correlation of each location to a particular analyte and thereby deriving the identity of the analyte in the sample. In sum, the location of the surface bound binding complexes is used to determine the identity of the one or more analytes of interest in the sample.

By way of further illustration, the following representative protein assay is summarized. Where one is interested in assaying a sample for the presence of 100 different proteins, an array displaying a collection of 100 different antibody binding agents is prepared, where each different antibody binding agents in the collection specifically binds to a different protein member of the 100 different proteins being assayed. The array is then contacted with the sample being assayed under conditions sufficient for binding complexes to be produced between the probe binding agent spots and their corresponding target proteins in the sample. Any resultant binding complexes on the surface of the array are then detected and the location of the detected binding complexes is used to determine which of the 100 proteins of interest is present in the sample.

In certain embodiments, two or more physiological sources, e.g., cell extracts, are assayed according to the above protocols in order to generate analyte profiles for the two or more sources that may be compared. In such embodiments, analyte containing sample may be separately contacted to identical arrays or together to the same array under binding conditions, depending on whether a means for distinguishing the patterns generated by the different populations of analytes is employed, e.g. distinguishable labels, such as two or more different emission wavelength fluorescent dyes, like Cy3 and Cy5, two or more isotopes with different energy of emission, like $^{32}P$ and $^{33}P$, gold or silver particles with different scattering spectra, labels which generate signals under different treatment conditions, like temperature, pH, treatment by additional chemical agents, etc., or generate signals at different time points after treatment.

In certain embodiments where 2 or more differentially labeled samples are assayed on the same array, e.g., in a two color differential protein expression analysis, the labeling/signal processing protocol described in U.S. Patent Application Ser. No. 60/324133 Methods and Compositions for Use in Multi-Color Array Analysis Applications (Ref No. CLON-083PRV; P-132) filed Sep. 21, 2001, the disclosure of which is herein incorporated by reference, is employed. In these embodiments, the first and second samples are initially divided into equal subpopulations, where each subpopulation is labeled with a different label. The resultant four different subpopulations are then paired so as to provide two pairs of subpopulations that are each made up of subpopulations of different samples and are distinguishably labeled. Each pair is then contacted with an array and a ratio of signal intensity for the analyte of interest of the first label to the second label for each pair is obtained, i.e., a first ratio for the first pair and a second ratio for the second pair is obtained. The first ratio is then divided by the second ratio to produce a final ratio, which is then compared to a set of a predetermined maximum and minimum significance values to at least qualitatively, if not semi-quantitatively, determine the amount of the analyte in the first sample relative to the amount of the analyte in the second sample. In many embodiments, the methods are employed to simultaneously determine the amount of multiples analytes in a first sample relative to a second sample. Also provided are systems and kits and algorithms for use in performing the subject methods. The subject methods and compositions find use in a variety of different applications, including genomic and proteomic differential expression analysis applications.

Kits

Also provided by the subject invention are kits for use in practicing the subject methods, as described above. The subject kits typically include an array of binding agents, as described above, i.e., an array of binding agents where each agent includes an epitope binding domain of an antibody. In addition, the subject kits may further include an incubation buffer, as described above, or at least components for making such a buffer, i.e., an incubation buffer that includes a metal ion chelating polysaccharide. The subject kits may also include an extraction/labeling buffer as described above, as well as one or more wash buffers. Also of interest are kits that include one or more label reagents for producing labeled analyte. In addition, the subject kits may include a fractionation means, e.g., where fractionated steps are employed, such as the binding agent/antibody columns described above. Furthermore, the kits may include one or more positive or negative controls, e.g., prelabeled antigen known to have a corresponding control spot on the array, etc.

In a preferred embodiment, the subject kits include two binding agent arrays, e.g., antibody arrays, that are generally identical. In addition, the kits of these embodiments include an extraction/labeling buffer, as described above. The kits also include a desalting buffer, such as the desalting buffer employed in the Experimental section below. The kits also include a background reducer stock, e.g., comprising a metal ion chelating polysaccharide, and an incubation buffer stuck, which two compositions are combined during use to make an incubation buffer, as described above. In addition, the kits of these embodiments include the seven specific washing fluids described in the Experimental section, below. Furthermore, the kits of these embodiments typically include a binding chamber in which the subject incubation step, as well as other steps, may be performed.

The various components of the kit may be present in separate containers or certain compatible components may be precombined into a single container, as desired.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Systems

Also provided are systems for use practicing the subject methods. The subject systems include at least the arrays described above, and a detector device for detecting surface bound complexes following incubation. The subject systems may also include additional components necessary for practicing a given embodiment of the subject methods, e.g., incubation buffer, extraction/labeling buffer, washing fluid, labeling reagents, etc., as described above.

Utility

The subject methods find use in a variety of different applications, where representative applications of interest include analyte detection, drug development, toxicity testing, clinical diagnostics, differential protein expression analysis, etc.

One application of particular interest in which the subject invention finds use is proteomics, in which the subject methods are used to characterize the proteome or some fraction of the proteome of a physiological sample, e.g. a cell, population of cells, population of proteins secreted by a cell or population of cells, etc. By proteome is meant the total collection or population of intracellular proteins of a cell or population of cells and the proteins secreted by the cell or population of cells. In using the subject methods in proteomics applications, the subject methods are employed to measure the presence, and usually quantity, of the proteins which have been expressed in the cell of interest, i.e., are present in the assayed physiological sample derived from the cell of interest. In certain applications, the subject methods are employed to characterize and then compare the proteomes of two or more distinct cell types, e.g., a diseased and normal cell. Proteomics applications in which the subject invention finds use are further described in WO 00/04382, WO 00/04389 and WO 00/04390, and the priority U.S. patent applications on which these international applications are based, the disclosures of which priority applications are herein incorporated by reference.

The following examples are offered by way of illustration and not by way of limitation.

EXPERIMENTAL

I. General

A. Solid Phase Chemistry and Immobilization of Primary Ab on Flat Surfaces

1. Activation Chemistries a. Non Covalent Chemistry.

i. Direct Immobilization on Mixed Hydrophobic/Hydrophilic Chains (C18-Tertiary Amine)

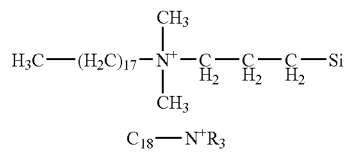

ii. Affinity Immobilization on Covalently Attached Protein A b. Covalent Chemistry i. PDITC Chemistry

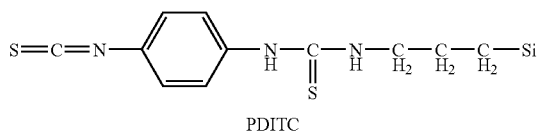

PDITC ii. DVS Chemistry

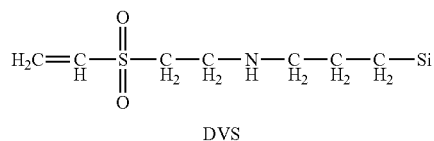

DVS

DVS chemistry provides stable immobilization, very low background signal, is not labor intensive and can be automated. Activated glass slides have been stored for more than 40 days without appreciable decrease in the immobilization capacity.

c. Comparison of DVS and PIDTC

DVS and PIDTC activated glass slides were printed with TaqStart (Clontech) antibody according to the following legend:

|   | D<br>Ab + 5% dextract | C<br>Ab + 5% glycerol | B<br>Ab + 1% Glycerol | A<br>Ab + NaCarbonate pH 9.3 |
|---|---|---|---|---|
| 1 | Ab + 5% dextract<br>196 μg/ml ab | Ab + 5% glycerol<br>196 μg/ml ab | Ab + 1% Glycerol<br>196 μg/ml ab | Ab + NaCarbonate<br>pH 9.3<br>196 μg/ml ab |
| 2 | Ab + 5% dextract<br>2.98 μg/ml ab | Ab + 5% glycerol<br>2.98 μg/ml ab | Ab + 1% Glycerol<br>2.98 μg/ml ab | Ab + NaCarbonate<br>pH 9.3<br>2.98 μg/ml ab |
| 3 | Ab + 5% dextract<br>3.49 μg/ml ab | Ab + 5% glycerol<br>3.49 μg/ml ab | Ab + 1% Glycerol<br>3.49 μg/ml ab | Ab + NaCarbonate<br>pH 9.3<br>3.49 μg/ml ab |
| 4 | Ab + 5% dextract<br>4.24 μg/ml ab | Ab + 5% glycerol<br>4.24 μg/ml ab | Ab + 1% Glycerol<br>4.24 μg/ml ab | Ab + NaCarbonate<br>pH 9.3<br>4.24 μg/ml ab |
| 5 | Ab + 5% dextract<br>5.12 μg/ml ab | Ab + 5% glycerol<br>5.12 μg/ml ab | Ab + 1% Glycerol<br>5.12 μg/ml ab | Ab + NaCarbonate<br>pH 9.3<br>5.12 μg/ml ab |

-continued

| | D<br>Ab + 5% dextract | C<br>Ab + 5%<br>glycerol | B<br>Ab + 1%<br>Glycerol | A<br>Ab + NaCarbonate<br>pH 9.3 |
|---|---|---|---|---|
| 6<br>6.6 µg/ml ab | Ab + 5% dextract<br>6.6 µg/ml ab | Ab + 5%<br>glycerol<br>6.6 µg/ml ab | Ab + 1%<br>Glycerol<br>6.6 µg/ml ab | Ab + NaCarbonate<br>pH 9.3<br>6.6 µg/ml ab |

After printing, the glass slides were stored for 3 weeks at 4° C. in 1% glycerol before proceeding with secondary binding with Cy3 labeled AdvanTaq (Clontech). The results of the binding assays are provided in FIG. 1, showing that DVS activated slides provide less background that PIDTC activated slides.

B. Immobilization of Ab

1. Manual Contact Printing

One coupling buffer has been studied with various additives for stabilization of the antibodies. Buffers with lower pH value have already been tested with DNA and RNA and provide stable immobilization. TaqStart antibody (Clontech) was used as a model system with Cy3 labeled AdvanTaq (Clontech) as antigen.

Printing Conditions:
0.1 M sodium carbonate pH 9.3.
0.1 M sodium carbonate pH 9.3 containing 1% glycerol.
0.1 M sodium carbonate pH 9.3 containing 5% glycerol.
0.1 M sodium carbonate pH 9.3 containing 5% dextran.

Figure 2:
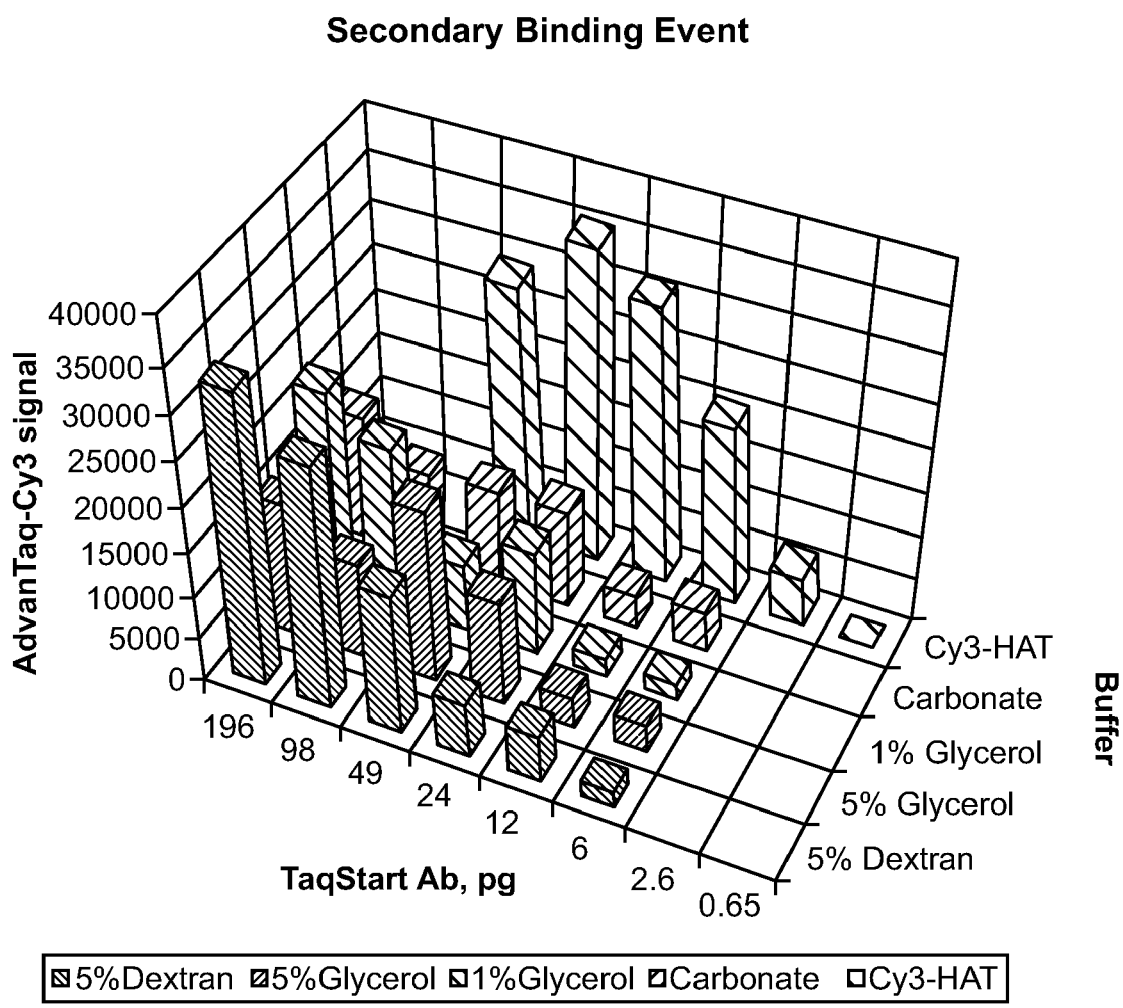
FIG. 2 provides a graphical representation of the different results obtained when different coupling conditions are employed for antibody immobilization.

From these four buffers the one with 5% dextran was the best possible buffer resulting in good linear dependence of the quantity of bound antigen as a function of quantity of immobilized antibody. The results are shown graphically in FIG. 2.

2. Stability of Immobilized Ab

TaqStart glass slides were stored for 20 days in TST buffer (10 mM Tris; 150 µM NaCl; 0.075% Tween 20; pH 7.3) containing 1% glycerol were titrated with 100 ng/mL Cy3 labeled AdvanTaq. There was no deviation in the signal from bound Cy3 labeled AdvanTaq to fresh and stored slides.

Alternatively, the slides were stored at 4° C. in 1% BSA (TST buffer) for over 3 weeks with similar results.

Figure 3:
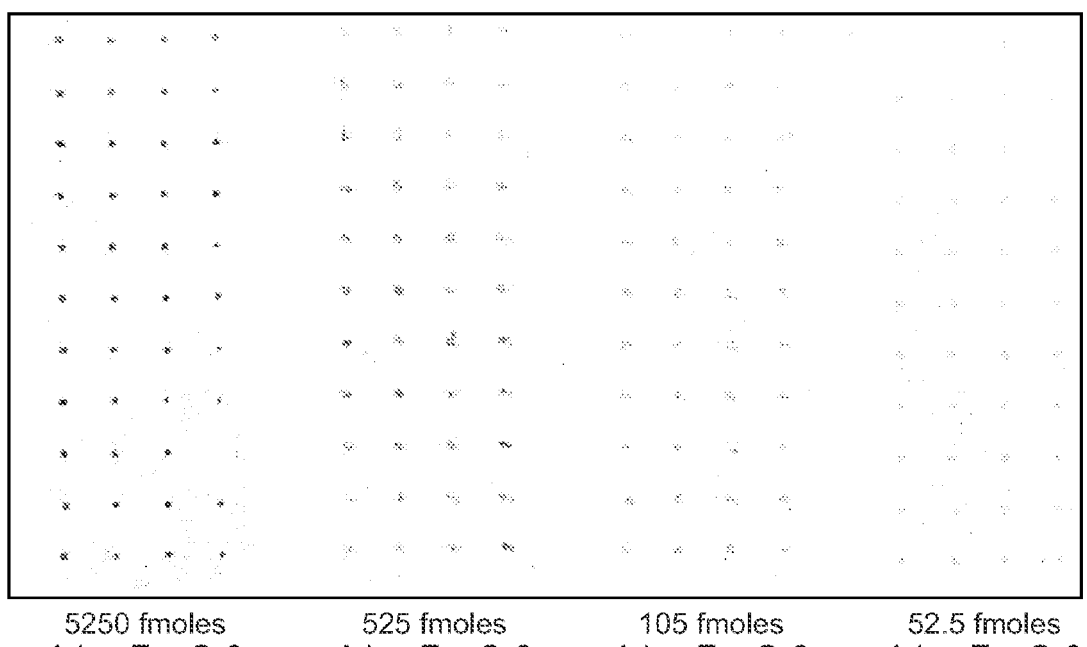
FIG. 3 is a computer generated image showing the results obtained with different amounts of a fluorescently labeled analyte.

3. The dependence of the signal of bound antigen from the quantity of Cy3 labeled antigen was studied with the TaqStart/AdvanTaq pair (binding again performed in 3% BSA in TST buffer). Specifically, 54.6 fmoles of Cy3-labeled AdvanTaq was incubated with a total of 44 spots of TaqStart antibody/slide (1.24 fmoles/spot). After blocking in 5 ml of 3% BSA in TST buffer the quantities of AdvanTaq-Cy3 denoted above were added in 5 µl volume to the blocking solution and mixed for 1 hour. After 3×5 minutes wash with ST buffer, the slides were dried and scanned at 80/90 power to sensitivity setting. The results are provided in FIG. 3 and shows that highly sensitive results were obtained.

4. Selectivity Assay

A polyclonal GFP (green fluorescent protein) Ab was tested next after affinity purification on Protein A. It was found that approximately 10% of the total IgG has affinity for GFPuv and it was immobilized side by side with TaqStart antibody.

Figure 4A:
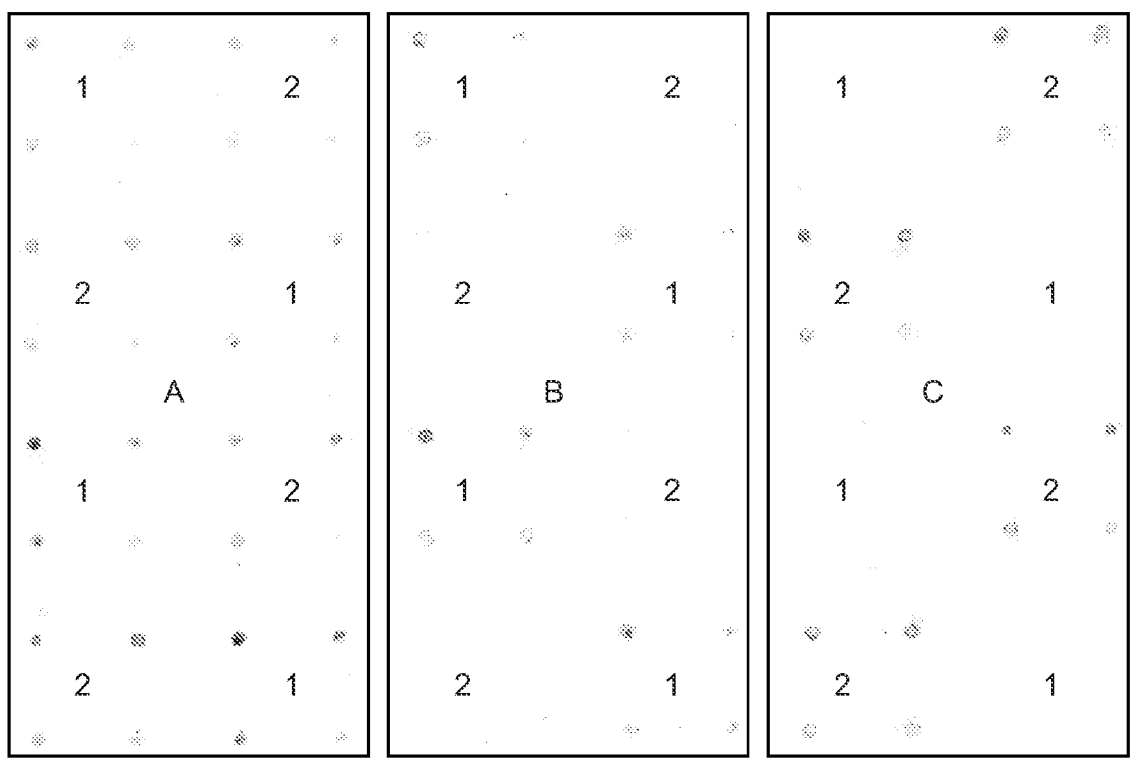
FIGS. 4A and 4B provide the results of selectivity and blocking assays described in the experimental section, below.

It was determined that each antibody retains its selectivity for the antigen as shown in FIG. 4A. In FIG. 4A, each block of 4 spots around the number is the serial dilution of the antibody spotted on the glass: 1. spots of TaqStart monoclonal antibody at 100, 50, 25 and 10 pg/nl; 2. spots of GFP polyclonal antibody at 660, 330, 115 and 66 pg/nl.

Panel A-slide exposed to a mixture of Cy3 labeled AdvanTaq (70 ng/ml) and GFPuv (104 ng/ml) in a total of 5 ml of 3% BSA in TST buffer for 1 hour, washed briefly with 3×5 min of TST buffer and scanned for Cy3 signal.

Panel B-slide exposed to Cy3 labeled AdvanTaq (70 ng/ml) in a total of 5 ml of 3% BSA in TST buffer for 1 hour, washed briefly with 3×5 min of TST buffer and scanned for Cy3 signal.

Panel C-slide exposed to Cy3 labeled GFPuv (104 ng/ml) in a total of 5 ml of 3% BSA in TST buffer for 1 hour, washed briefly with 3×5 min of TST buffer and scanned for Cy3 signal.

The above results again demonstrate the selectivity achieved with the subject assays.

C. Development of Efficient Blocking of the Residual Active Groups on the Solid Phase.

The use of 3% BSA in TST results in satisfactory blocking of the residual active groups on the glass surface. 3% BSA is fairly efficient for blocking Cy3 and Cy5 labeled proteins on DVS activated glass surfaces. Preliminary attempts to use diamino-PEG 500 for blocking were not successful due to very strong background on PDITC glass and fairly strong background on DVS glass (not shown).

Dry milk was also used successfully. Additional blocking agents of interest include ethanolamine or other low molecular weight components for blocking.

4. Blocking and incubation in 0.5% dry milk is as efficient as 1% BSA. Increase of the concentration of the dry milk to 2% results in a strong decrease of the signal detected from the slides. See e.g., FIG. 4B.

Figure 4B:
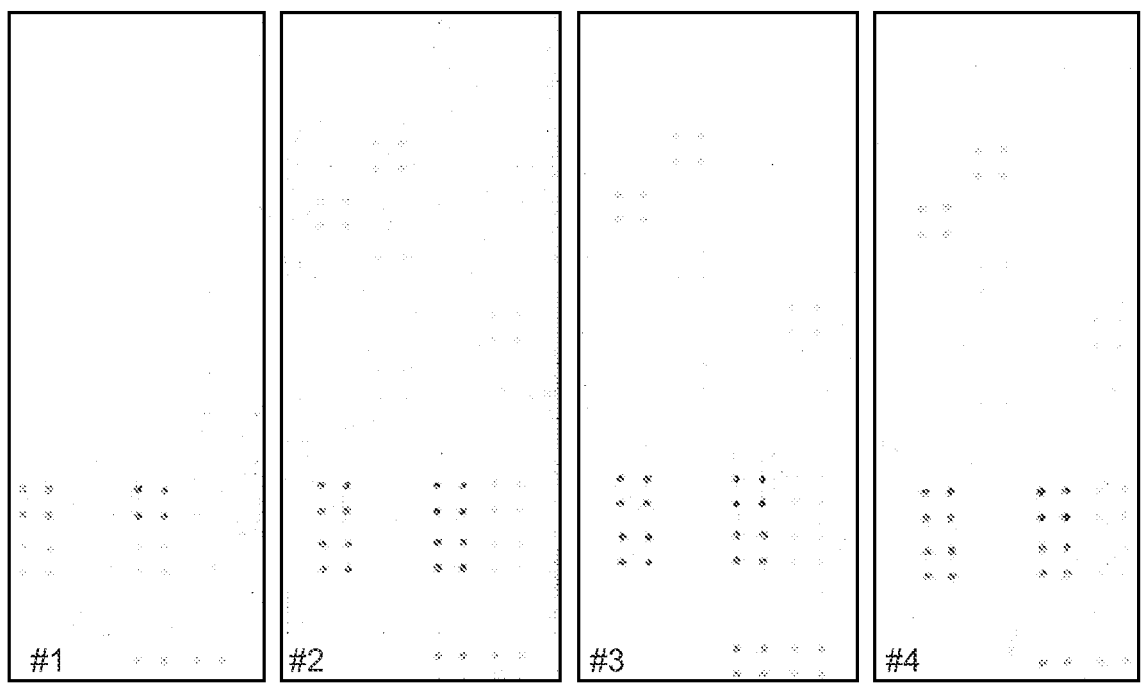

In FIG. 4B, each slide was blocked for 1 hour at ambient temperature as follows:
1: 5 ml of sterile filtered 2% dry milk solution in TST;
2: 5 ml of sterile filtered 1% dry milk solution in TST;
3: 5 ml of sterile filtered 0.5% dry milk solution in TST;
4. 5 ml of sterile filtered 1% BSA solution in TEST.

Incubation was carried out for 30 min at ambient temperature with slides 1 to 3 being incubated with 2 µl of Cy3-& 2 µl of Cy5 AdvanTaq and GFPuv plus 20 µl of Ag Mix-Cy3. Slide 4 was incubated with the same quantities, but the Ag Mix-Cy3 was pre filtered through 0.22 µm filter. Washing was performed with 5×5 ml of TST buffer (2 minutes each).

D. Array of Antibodies

An antibody array according to the legend shown in FIG. 5 was prepared and tested as follows.

1. Preparation

A total of 22 different antigens as listed in the Table below were mixed in equimolar ratio and labeled with Cy3 or Cy5 reporter labels. The antibodies corresponding to these antigens were deposited on DVS activated glass slides (Beckman contact printer) utilizing 200 µm pins. Some of the antibodies were dialyzed, while some were just diluted in order to investigate the effect of excessive glycerol on the immobilization project.

Table of antibodies

| Number | Antibody |
|---|---|
| 1 | AdvanTaq-TaqStart |
| 2 | b-catenin |
| 3 | bax |
| 4 | Calnexin |
| 5 | Calretinin |
| 6 | CaM kinase IV |
| dial. 7 | cask |
| dial. 8 | CD45 |
| 9 | CDC27 |
| dial. 10 | contactin |
| 11 | CRP-1 |
| 12 | Dematin |
| 13 | DFF45 |
| dial. 14 | Integrin a5 |
| dial. 15 | Janusin |
| 16 | LRP |
| dial. 17 | MAP2B |
| dial. 18 | MAP4 |
| dial. 19 | mGluR1 |
| dial. 20 | Neuroglycan C |
| 21 | PSD-95 |
| 22 | R-NCAM |
| dial. 23 | Thrombospondin-1 |
| 24 | GFP poly |

Figure 6A:
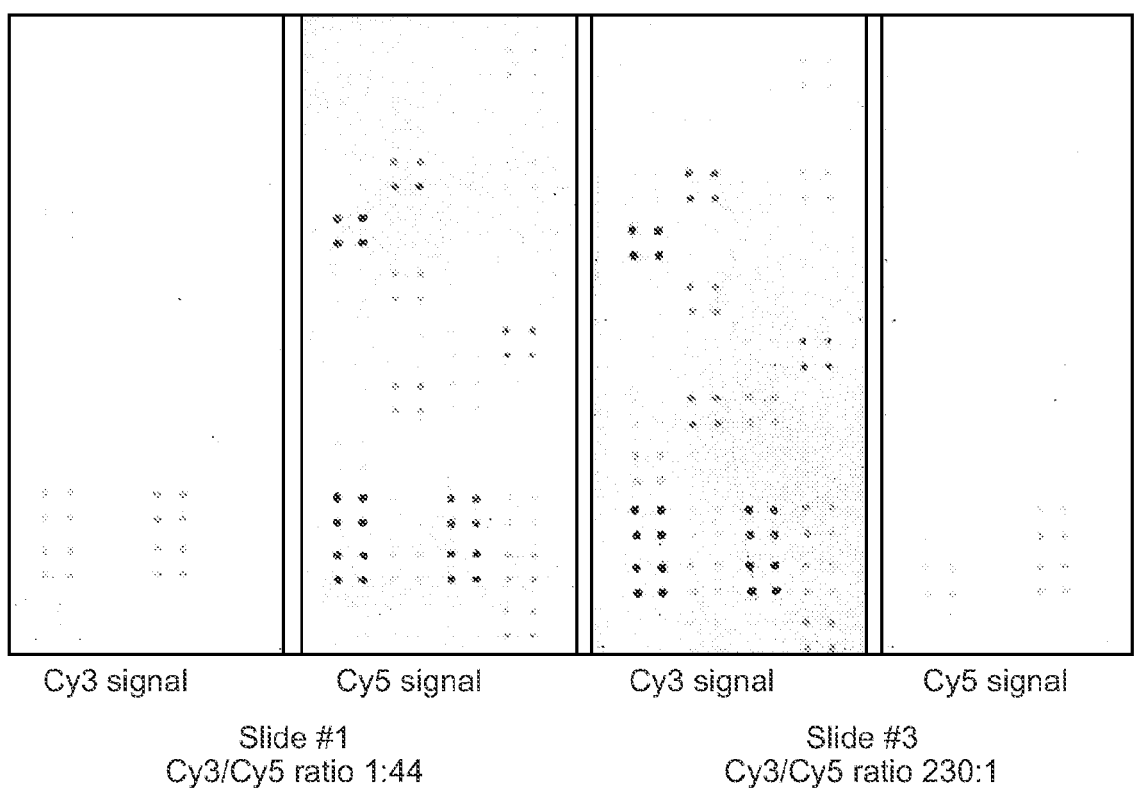
FIGS. 6A to 6D provide the results of various assays performed with the array shown in FIG. 5.
Figure 6B:
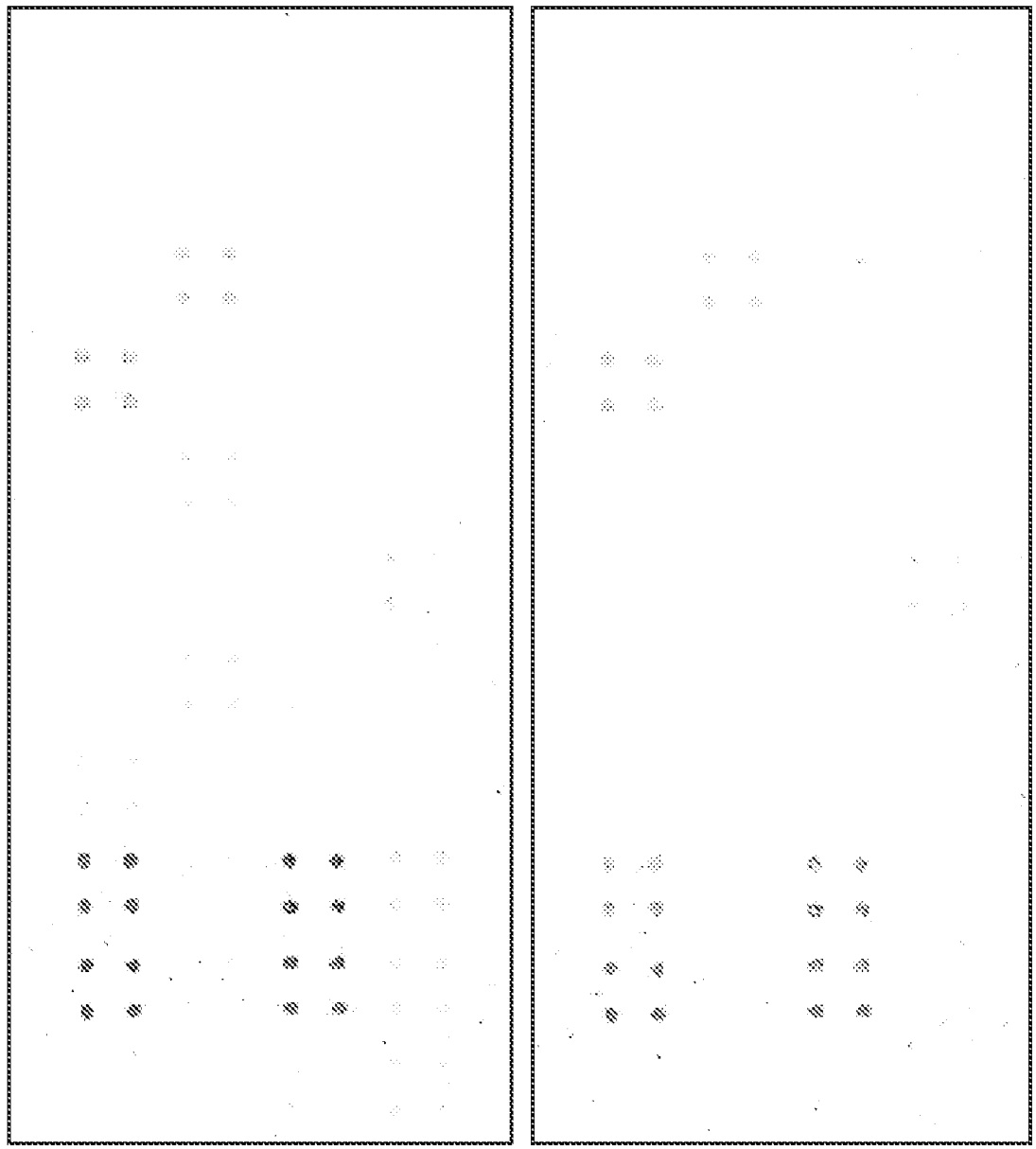
Figure 6C:
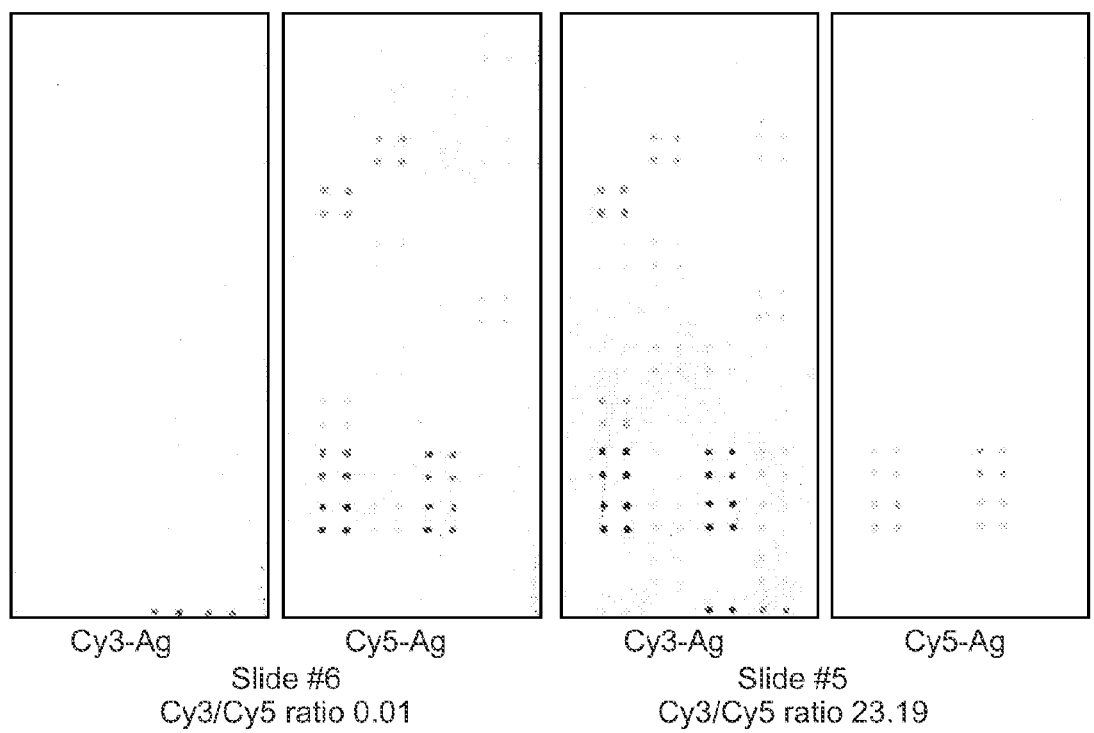

2. Testing and Results:

The positioning and the immobilization conditions are shown in FIG. 5 and the table above. Different ratios of Cy3/Cy5 labeled Ag mixture were incubated either with 1% BSA or various concentrations of dry milk (all in TST buffer), the non adsorbed Ag was washed away with 5×5 mL of TST buffer for 2 minutes each and the slides were scanned. The results are provided in FIGS. 6A; 6B; and 6C. The results from these experiments can be summarized as follows: 1. There is a concern about the reproducibility of protein deposition by contact printing—the SD as a % of the average signal from 4 repeat spots can be as high as 200%. Additional concern is the inability of the printer to deposit spots at certain positions at all (for an example TaqStart (AdvanTaq Ab) was deposited only on one slide of 20 and dialyzed CD45 Ab was not deposited at all. The highest variability occurs with Ab which were spotted in presence of high concentrations of glycerol. The glycerol presence results in a very slow (if any at al) drying of the spotted material. 2. Presence of glycerol at concentrations above 1% is detrimental to the immobilization efficiency. Additional dilution of the 20% glycerol starting solution to 4% results in immobilization of sufficient quantity of Ab to detect a signal from Cy3 or Cy5 labeled Ag.

Figure 6D:
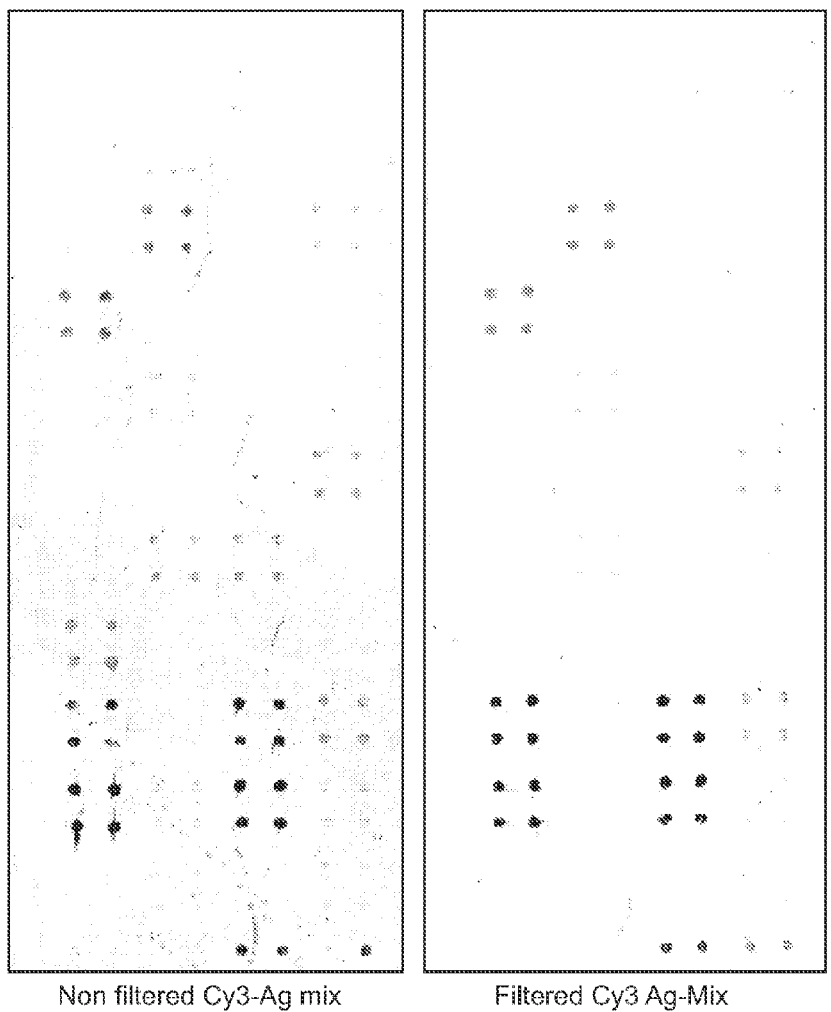

3. There is a significant difference in the signal obtained from non filtered and filtered Cy3 labeled Ag mixture. Two of the antigens were completely removed during the filtration. A surprising result is that one of the antigens (BAX) can be detected in the filtered sample, while it is undetectable in the non filtered sample. This can be attributed to the significantly higher background detected from the slide incubated with non filtered Cy3 labeled Ag mix. The results are provided in FIG. 6D.

4. There is a correlation between the ratio of Cy3 to Cy5 labeled Ag mix with the detected signal. It is obvious that the correlation is not linear, but the strongest signals are at the level of saturation and scanning at lower laser energy and detector sensitivity might increase the dynamic range. So far we could say that there is close to linear correlation between loaded and detected ratios in the 100 fold range between 0.2 and 23 Cy3/Cy5 (see table below).

| | Loaded ratio Cy3/Cy5 Ag Mix | | | | | |
|---|---|---|---|---|---|---|
| | 0.01 | 0.02 | 0.23 | 2.32 | 23.19 | 230.00 |
| Ag name | Detected as % of loaded | | | | | |
| Calretinin | 200% | 174% | 116% | 41% | | 3% |
| CASK | 200% | 156% | 118% | 88% | 105% | 35% |
| CDC27 | 700% | 391% | 105% | 74% | 43% | 3% |
| DFF45 | 800% | 920% | 155% | 109% | 72% | 5% |
| Janusin | 700% | 674% | 271% | 171% | 137% | 11% |
| MAP2B | 100% | 280% | 211% | 177% | 75% | 42% |
| mGluR1 | 100% | 162% | 120% | 76% | 31% | 60% |
| Integrin a5 | 800% | 662% | 255% | 91% | 96% | 10% |
| MAP4 | 200% | 363% | 246% | 94% | 21% | 17% |
| Neuroglycan C | 100% | 209% | 181% | 89% | 34% | 14% |
| BAX | 500% | 255% | 45% | 29% | | |
| Calretinin | 200% | 181% | 105% | 75% | 88% | 23% |
| CDC27 | 700% | 374% | 133% | 91% | 63% | 14% |
| DFF45 | 800% | 339% | 156% | 118% | 107% | 29% |
| MAP2B | 700% | 686% | 144% | 94% | 41% | 6% |
| mGluR1 | 500% | 426% | 142% | 63% | 47% | 6% |
| PSD95 | 1000% | 1541% | 193% | | 64% | 5% |
| Beta-Catenin | 300% | 355% | 41% | 21% | 16% | 3% |
| CaM Kinase IV | 600% | 487% | 67% | 36% | 38% | 5% |
| Dematin | 1000% | 134% | 82% | 39% | 51% | 16% |
| MAP4 | 1400% | 668% | 242% | 159% | 68% | 14% |
| Neuroglycan C | 1100% | 420% | 193% | 101% | 50% | 8% |
| R-NCAM | 1300% | 352% | 194% | 88% | 70% | 14% |

Figure 7:
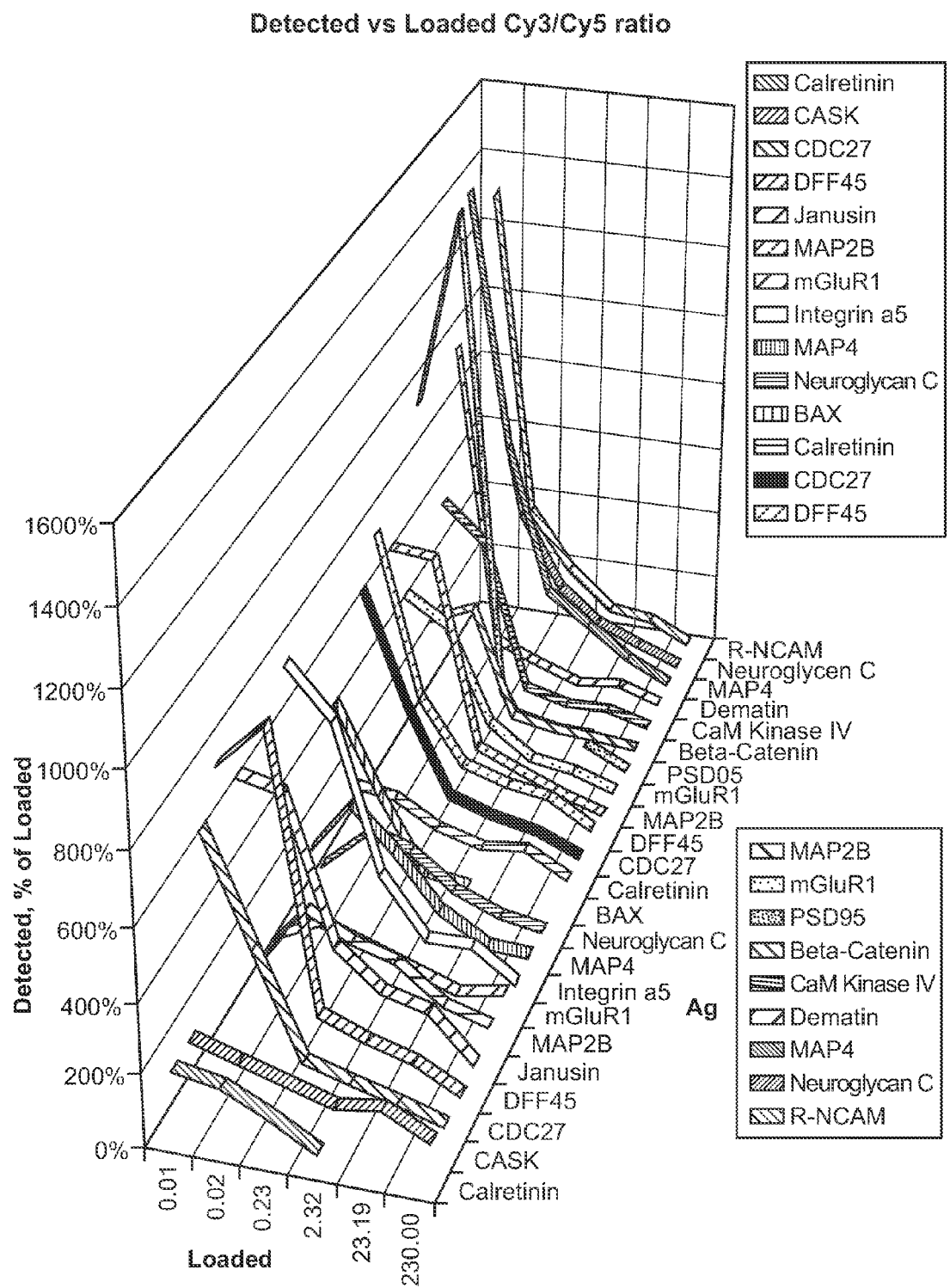
FIG. 7 provides graphical results of a two color assay reported in the experimental section, below.

The above results are also provided graphically in FIG. 7.

II. General Section Two

A. Solid Phase Chemistry and Immobilization of Primary Ab on Glass Surfaces

1. Activation Chemistries

Figure 8:
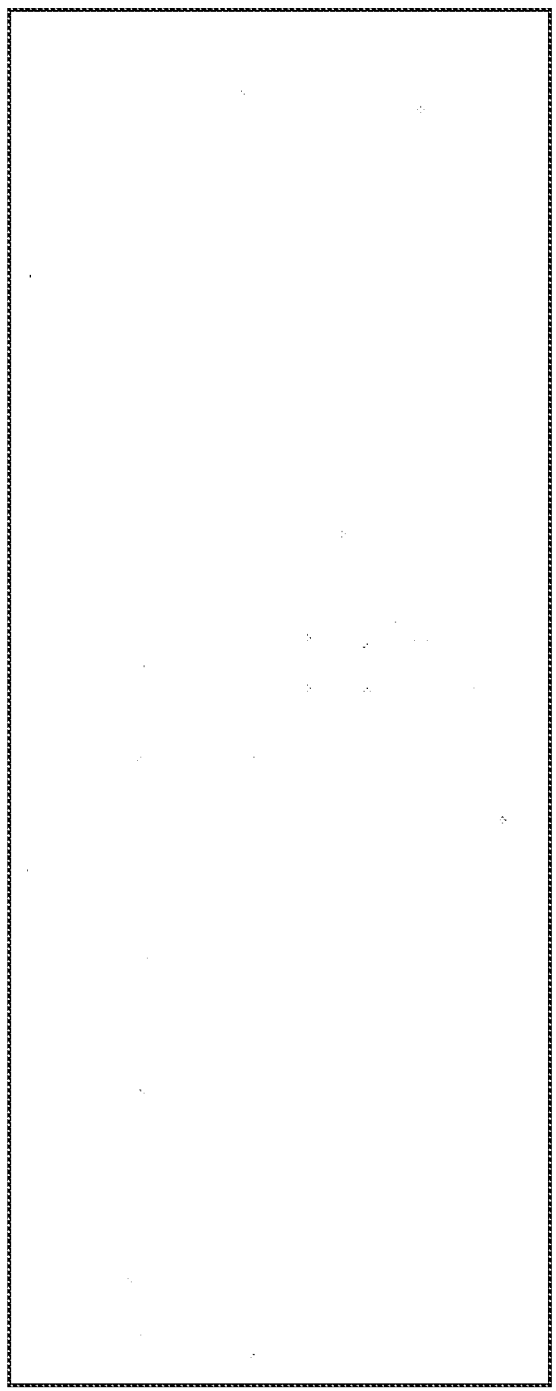
FIG. 8 provides a comparison of results obtained with 3D link slides and DVS slides.
Figure 8:
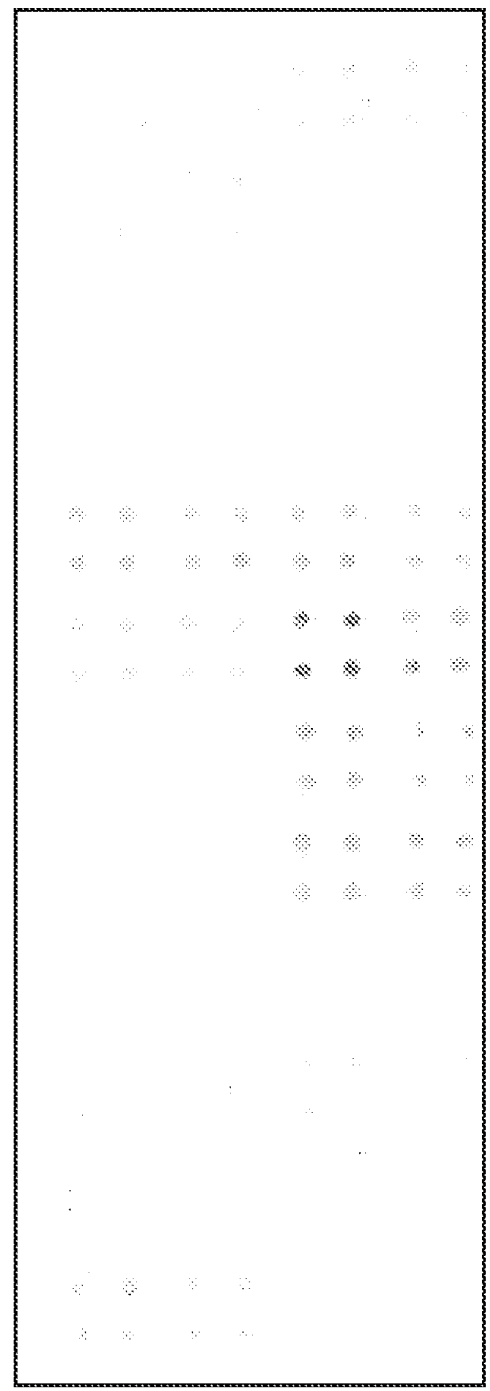

3D-Link activated glass slides were compared with DVS chemistry:

3D-Link chemistry is not disclosed, but according to communication with the vendor is based on active ester groups. Antibody preparations were spotted and the intensity of the signal obtained from pre-labeled antigens was detected as shown in FIG. 8. Both 1% albumin in TST or 3D-Link blocking solution (in 0.1 M Tris; 50 mM ethanolamine) gave similar ratios of signal and noise.

Figure 9:
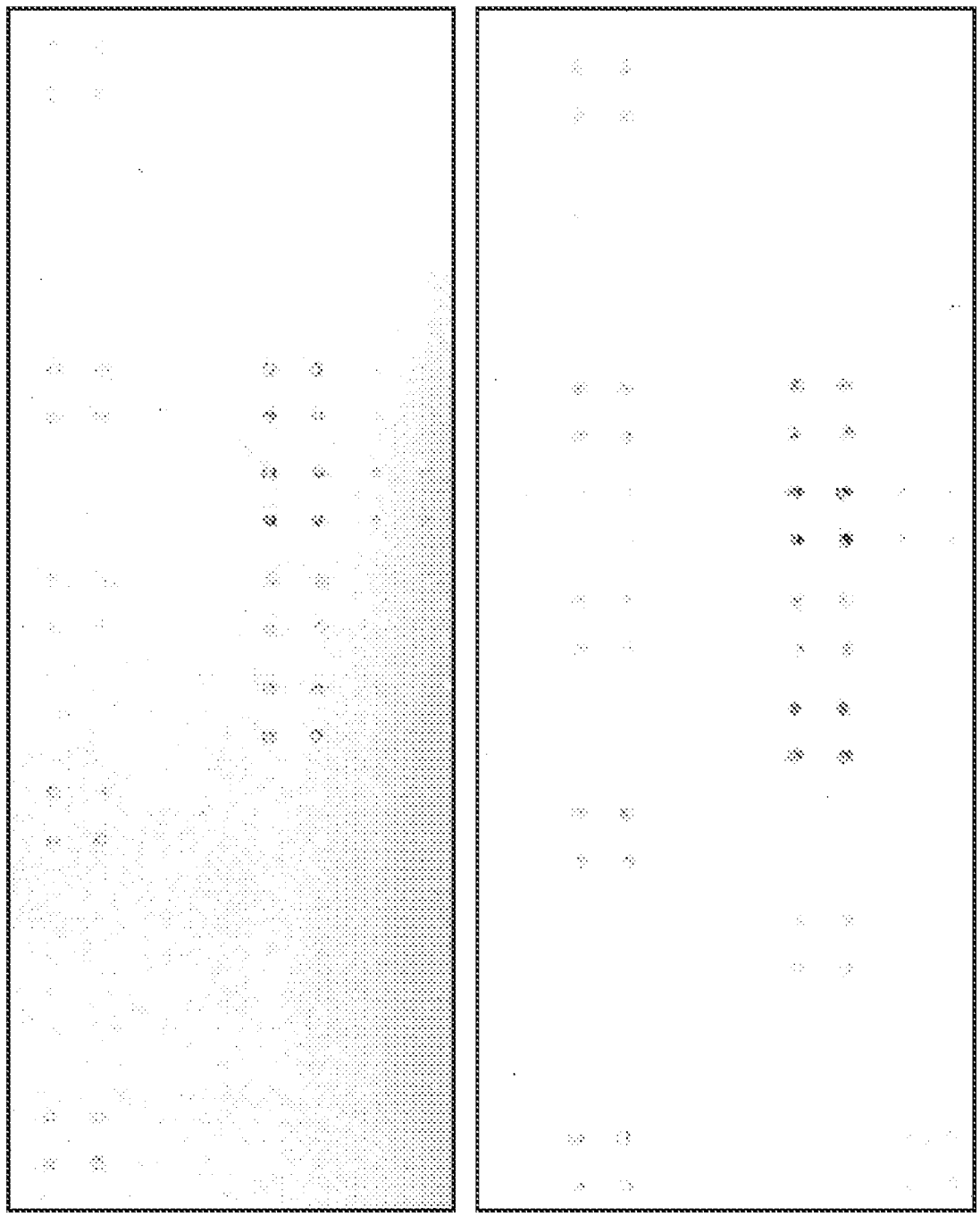
FIG. 9 provides a comparison of results obtained with Costar and Clontech aminated glass slides activated with DVS.

2. Two types of aminated glass slides were compared—Costar and Clontech. Both types were activated with DVS, spotted with the same antibody set and incubated with the same quantity of Cy3/Cy5 labeled antigens. Only the Cy3 signal is shown in FIG. 9. The position of the antibodies on the grid is the same in all slides and is presented in the table below. Each field of the table presenting antibody contains 4 repeats of the same antibody. Due to the low concentration of the initial antibody material, after dialysis some of the spotted antibodies were at a concentration of 10 μg/mL. MEKK3, DNA pol, p-Cadhedrin and CD5/VNRa antibodies did not have their respective antigens in the prelabeled antigen mixes (the antigens were delivered in 1% SDS solutions and were precipitating when we attempted transfer to the labeling buffer.

| AdvanTaq | AdvanTaq | DFF45 | DFF45 |
|---|---|---|---|
| b-Catenin | b-Catenin | Integrin a5 | Integrin a5 |
| BAX | BAX | Janusin | Janusin |

| -continued | | | |
|---|---|---|---|
| Calnexin | Calnexin | LRP | LRP |
| Calretinin | Calretinin | MAP2B | MAP2B |
| Cam Kinase IV | Cam Kinase IV | MAP4 | MAP4 |
| CASK | CASK | mGluR1 | mGluR1 |
| MEKK3 | MEKK3 | Neuroglycan C | Neuroglycan C |
| CDC27 | CDC27 | PSD-95 | PSD-95 |
| DNA pol d | DNA pol d | R-NCAM | R-NCAM |
| CRP-1 | CRP-1 | P-Cadherin | P-Cadherin |
| Dematin | Dematin | CD51/VNRa | CD51/VNRa |

The good result is that there appears to be no cross-talk (none of these antibodies showed any signal with the Cy3 and Cy5 labeled antigen mixes when their respective antigen was absent).

3. Optimization of Activation Chemistry—pH, Time for Activation, Quantity of Activator.

Figure 10:
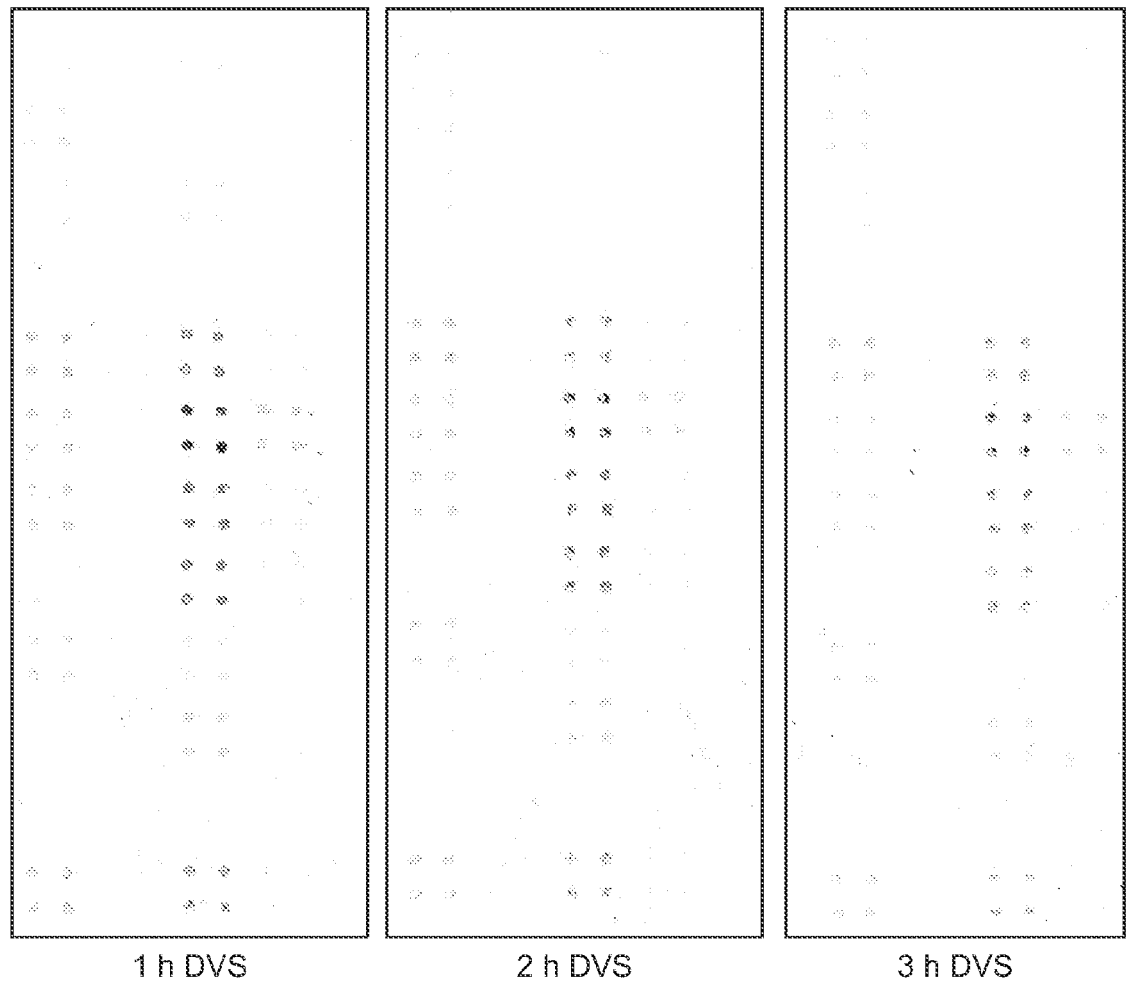
FIG. 10 provides a comparison of results obtained after different activation times.

Sets of glass slides were activated for 1, 2 and 3 h. After printing the same set of antibodies on all of them, the slides were incubated with the same quantities of pre-labeled antigens and the bound signal was detected. None of the variants showed any significant difference in signal, with the 1 hour activation having slightly higher signal and lower background. Only the Cy3 signal is shown in FIG. 10. In FIG. 10, the set of antibodies printed above contained GFPuv instead of CD5/VNRa down at the right corner. All other spots were the same as in the first table above.

B. Preparation of 3D Slides

The following scheme was utilized to prepare 3D slides:

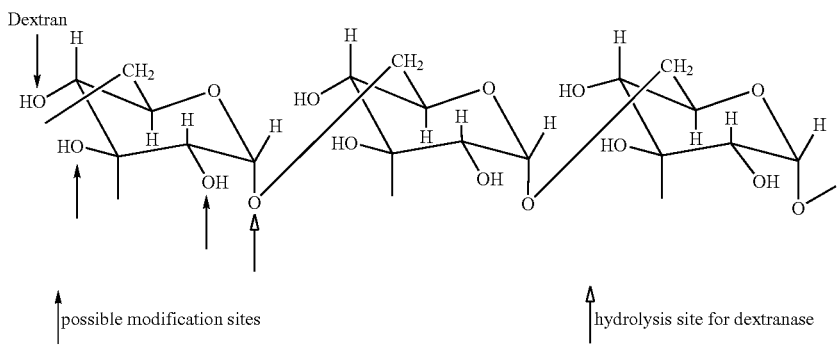

The crosslinked dextran of Sephadex G100 was activated with epichlorohydrin and reacted with ethylene diamine. The aminated Sephadex G100 was hydrolyzed with dextranase and resulted in soluble crosslinked dextran with an average MW around 60 kD. DVS activated glass slides were coated with this soluble dextran and the residual amino groups as shown in the figure below were activated by new treatment with DVS:

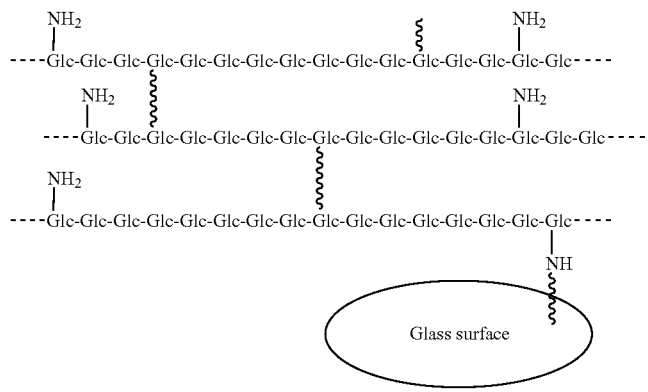

Figure 11:
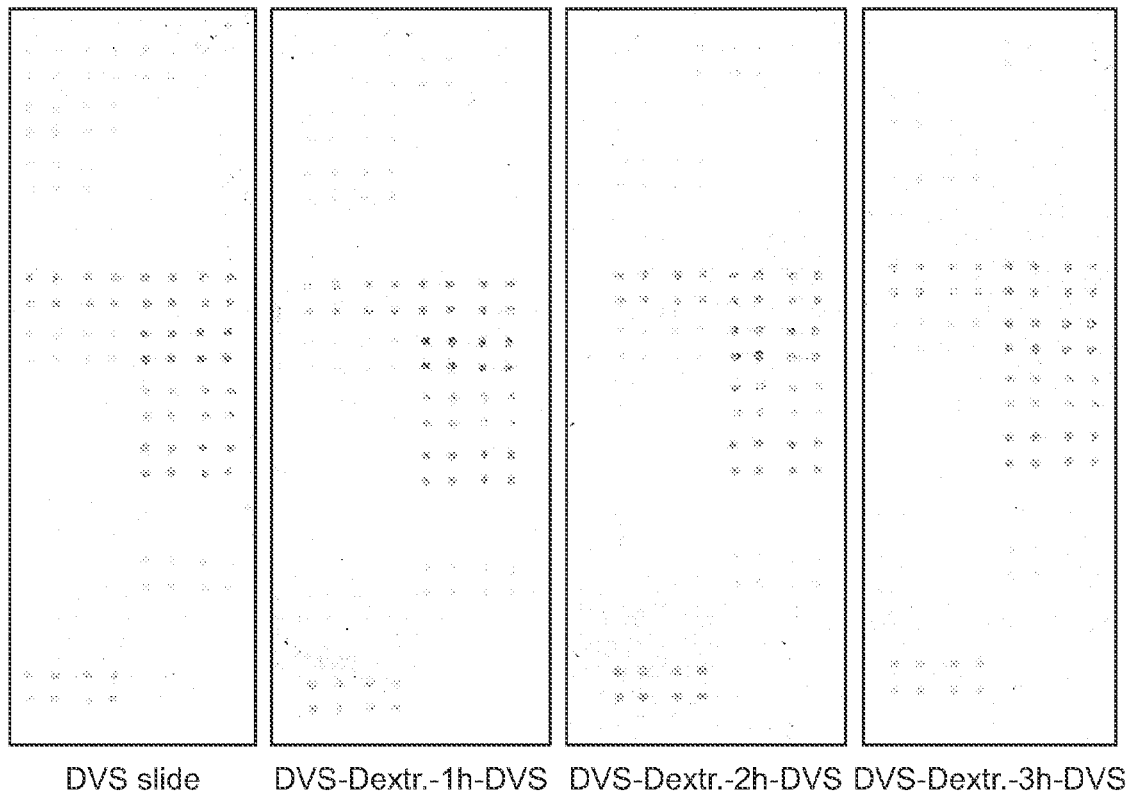
FIG. 11 provides the results obtained with a 3D slide according to the subject invention.

The same antibody set as described above was printed on primary DVS activated glass slides as well on slides coupled with amino dextran for 1, 2 and 3 hours. The amount of successfully immobilized antibodies was detected by incubation of the slides with a mixture of Cy3 and Cy5 labeled antigens and the results are shown in FIG. 11. (Only Cy5 signal is shown)

While there is no significant difference in the signal, it should be noted that the starting concentrations of the spotted antibodies are quite low (some of them are at a concentration of 10 µg/mL).

C. Sample Preparation

Several different protein extraction protocols were evaluated as below:
1. Carbonate buffer 1% Empigen pH 9.3
2. Carbonate buffer 0.8% ODG 0.2% NP40 pH 9.3
3. Phosphate buffer 1% Empigen pH 7.0
4. Carbonate buffer 1% Empigen 0.5% NP40 pH 9.3
5. Tris buffer 1% Empigen
6. Phosphate buffer 0.8% ODG 0.2% NP40 pH 7.0
7. TST buffer 1% Empigen pH 7.4
ODG stands for n-Octyl-β-D-Glucopyranoside All extracts were prepared from approximately 50 mg of cells in 1 mL of the respective buffer.

Tabulated additional data is presented below:

| Buffer | Cells, mg | Buffer, mL | Cell/buffer, w/v | Protein, mg/mL | Protein, mg | Protein/Cell, % | Cell state, before extr. |
|---|---|---|---|---|---|---|---|
| 1 | 123 | 1.5 | 82 | 2.91 | 4.37 | 3.55 | fresh |
| 1 | 115 | 1.5 | 77 | 3.2 | 4.80 | 4.17 | frozen |
| 2 | 108 | 1.5 | 72 | 2.82 | 4.23 | 3.92 | fresh |
| 2 | 97 | 1.5 | 65 | 2.6 | 3.90 | 4.02 | frozen |
| 3 | 51 | 1 | 51 | 2.76 | 2.76 | 5.41 | fresh |
| 4 | 49 | 1 | 49 | 2.48 | 2.48 | 5.06 | fresh |
| 5 | 57 | 1 | 57 | 2.25 | 2.25 | 3.95 | fresh |
| 3 | 55 | 1 | 55 | 3.17 | 3.17 | 5.76 | frozen |
| 6 | 54 | 1 | 54 | 3.05 | 3.05 | 5.65 | frozen |
| 1 | 53 | 1 | 53 | 3.1 | 3.10 | 5.85 | frozen |
| 2 | 51 | 1 | 51 | 2.89 | 2.89 | 5.67 | frozen |
| 7 | 53 | 1 | 53 | 3.1 | 3.10 | 5.85 | frozen |

Figure 12:
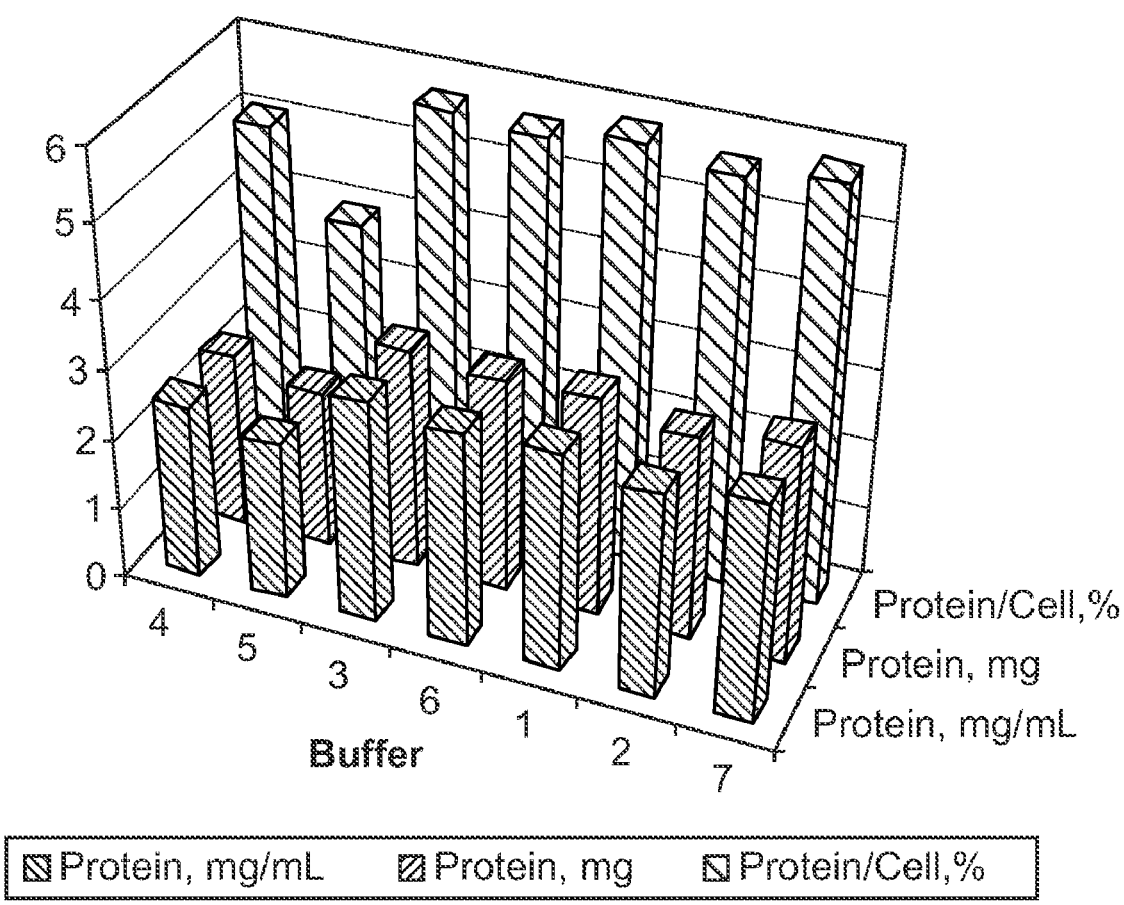
FIG. 12 provides the results obtained using different extraction protocols.

The type of buffer is the same as in the figure above.
The results are provided in FIG. 12.

Figure 13:
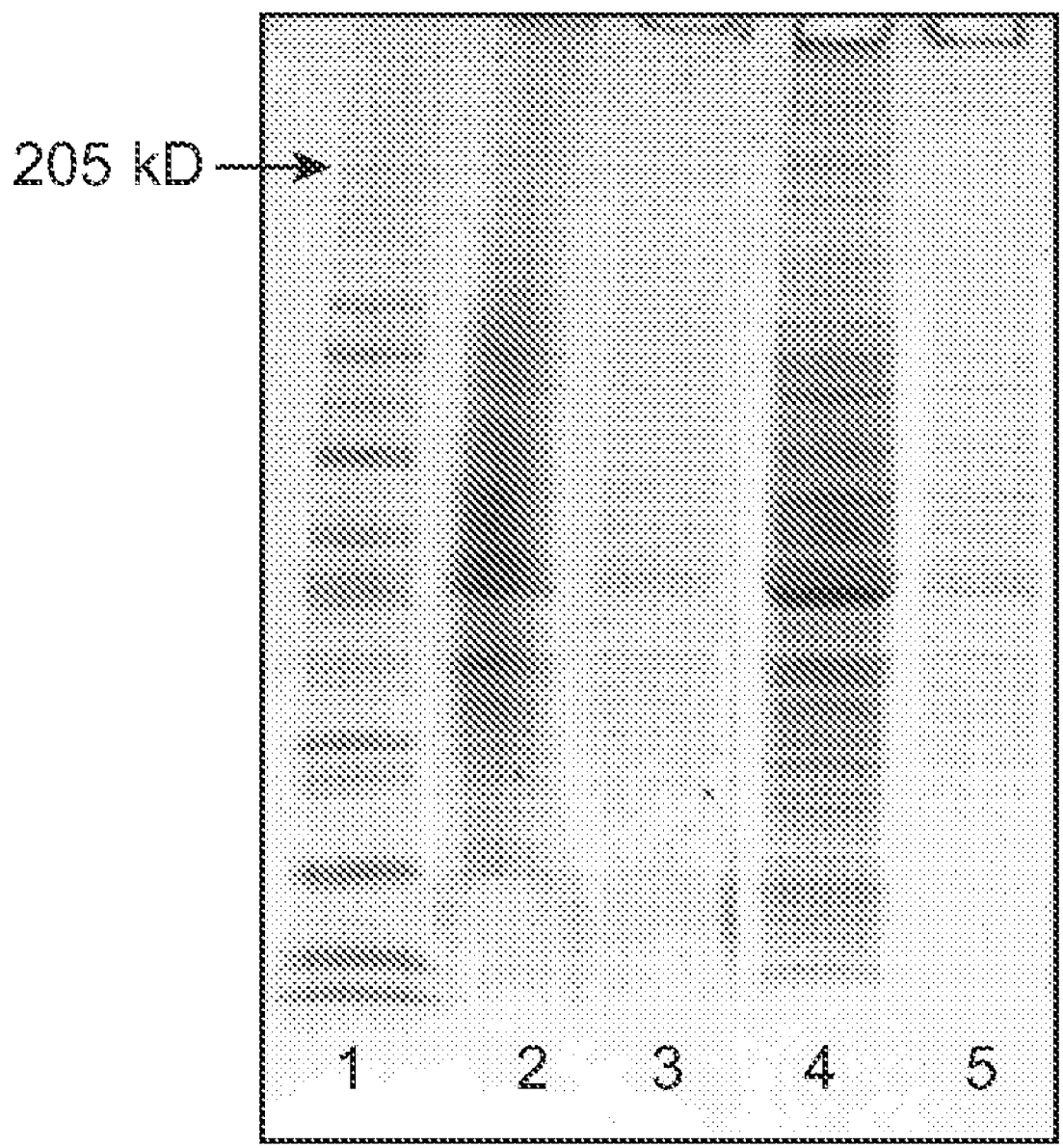
FIG. 13 provides a depiction of an SDS gel showing the results obtained using various extraction protocols.

Based on UV absorbance data (280 nm) it appears that the Empigen extract contains approximately 6% more protein than the ODG/NP-40 extract. Unfortunately, the behavior of the Empigen extract on SDS gels presents a problem for further analyses. Specifically, it is almost impossible to see the distribution of low molecular weight components from the Empigen extract. Further attempt will be made to desalt the sample, but it might result in loss of protein components. The protein quantity in the high molecular weight region points out that ODG/NP-40 is more efficient in extraction of large proteins (this is confirmed also by the analytical SEC runs of both extracts). See FIG. 13. In FIG. 13, the lanes are as follows:
1. Broad MW standards (from 205 down to 6 kD)
2. Empigen extract:2
3. Empigen extract:10
4. ODG/NP-40 extract:2
5. ODG/NP-40 extract:10

D. Filtration and its Influence on Background/Protein Yield:

Both labeled and non labeled HeLa cell extracts were subjected to filtration through 0.22 µm filters based on either Durapore (low protein binding PVDF membrane) or Nylon membrane. Very little material was retarded on the PVDF membrane. Approximately 15% of the non labeled HeLa extract was retarded on the Nylon membrane. Approximately 65% of the labeled protein was retarded on the Nylon membrane.

E. Labeling of Complex Biological Mixtures

The extracts prepared at pH 9.3 (buffers 1 & 2) were labeled with Cy 3 and Cy5. After desalting the extracts were analyzed by analytical SEC and SDS electrophoresis. It is important to point out that with the Empigen extraction buffer, the 550 nm absorbance profile (Cy3 absorbance maximum) is not following closely the 254 nm absorbance profile. This is an indication for uneven substitution of the components of the extract. In addition, the peak at 68.470 min which is a component(s) retarded non specifically on the SEC column is also labeled much more strongly compared to the rest of the rest of the components—this is the most obvious example. Judging from the retardation after the total volume of the column, this component(s) is very hydrophobic. The above results were not observed with the ODG/NP-40 extraction buffer.

F. Both types of extracts (i.e., Empigen; ODG/NP-40) before and after labeling were incubated with DVS glass slides printed with the following set of antibodies:

| | | | |
|---|---|---|---|
| AdvanTaq | AdvanTaq | DFF45 | DFF45 |
| b-Catenin | b-Catenin | Integrin a5 | Integrin a5 |
| BAX | BAX | Janusin | Janusin |
| Calnexin | Calnexin | LRP | LRP |
| Calretinin | Calretinin | MAP2B | MAP2B |
| Cam Kinase IV | Cam Kinase IV | MAP4 | MAP4 |
| CASK | CASK | mGluR1 | mGluR1 |
| MEKK3 | MEKK3 | Neuroglycan C | Neuroglycan C |
| CDC27 | CDC27 | PSD-95 | PSD-95 |
| DNA pol d | DNA pol d | R-NCAM | R-NCAM |
| CRP-1 | CRP-1 | P-Cadherin | P-Cadherin |
| Dematin | Dematin | CD51/VNRa | CD51/VNRa |

Each field contained 4 spots (2×2) of the corresponding antibody.

Figure 14A:
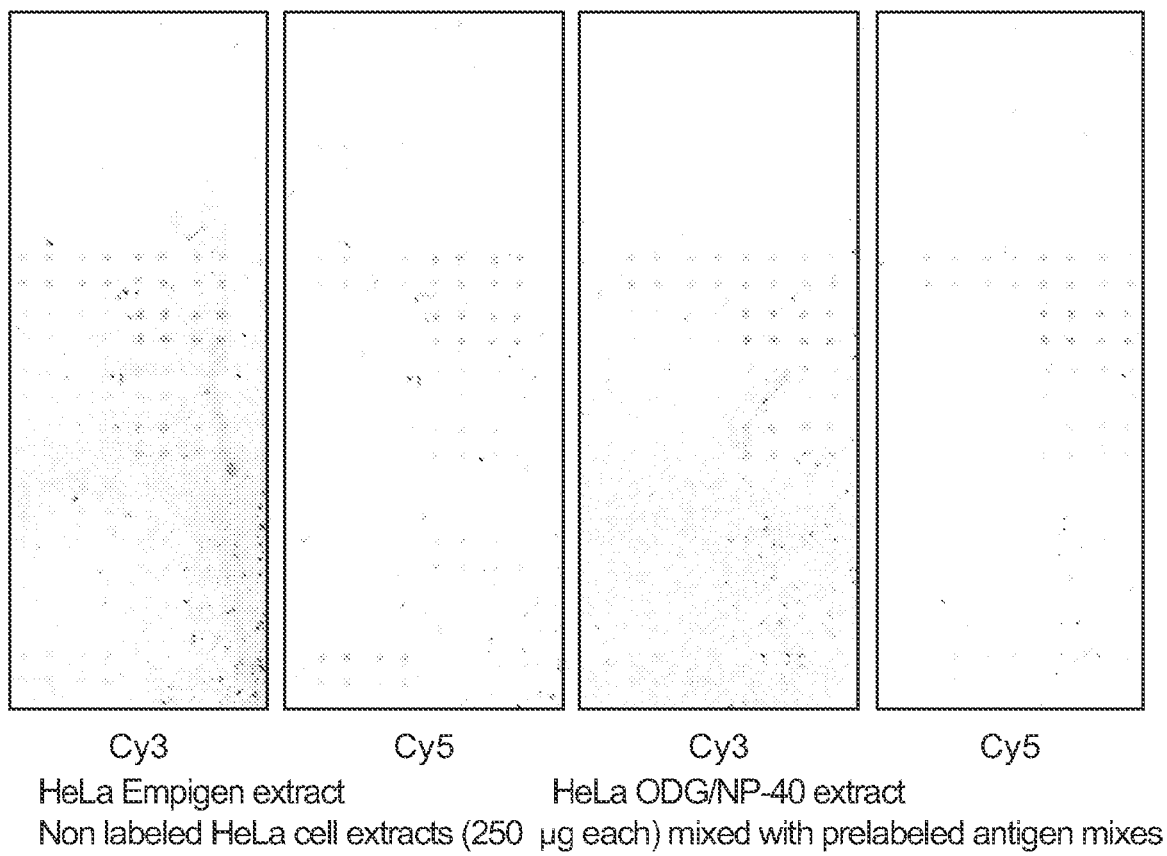
FIGS. 14A and B provide the results of an assay comparing the images obtained using different sample preparation protocols.
Figure 14B:
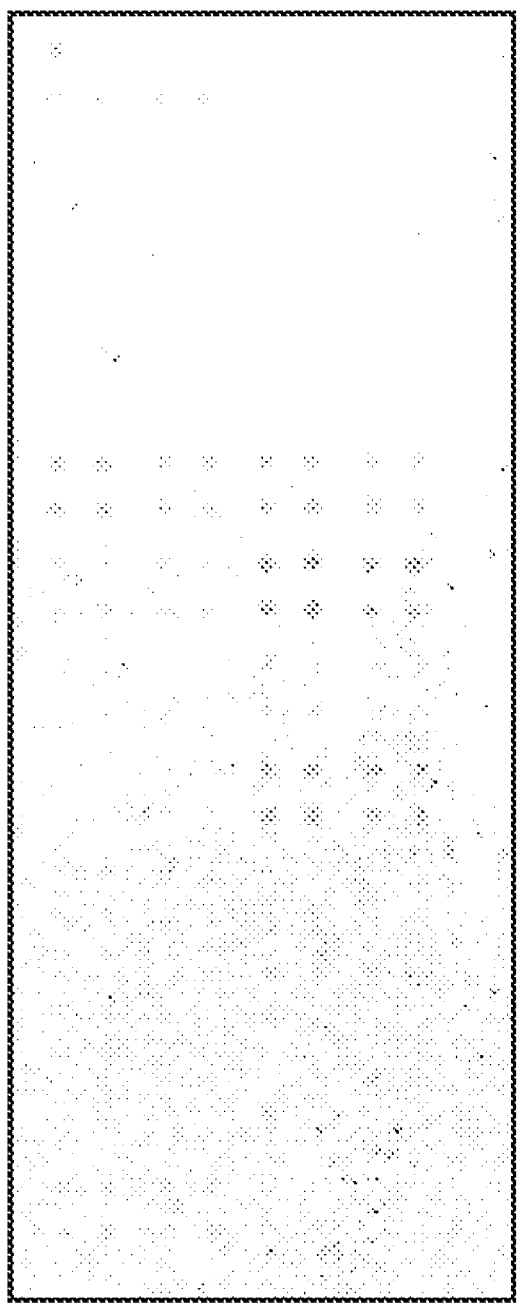
Figure 14B:
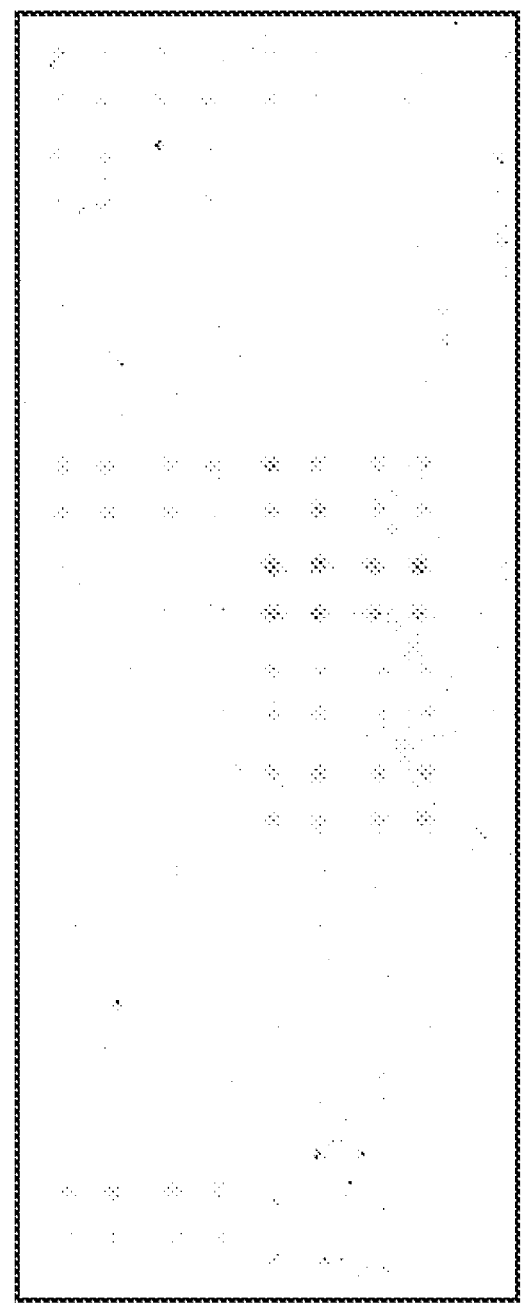

Non labeled HeLa extracts did not have significant autofluorescence. FIG. 14A provides the slides exposed to non labeled HeLa extracts in Empigen and ODG/NP-40 respectively in mixture with prelabeled antigens. FIG. 14B provides the control slide exposed to prelabeled antigens. It has to be pointed out that the Empigen extract appears to cause stronger background than the ODG/NP-40 extract. When either Empigen or ODG/NP-40 extracts were incubated with similar slides printed with antibodies without the prelabeled antigens, there was no background (an indication that some of the prelabeled antigens are binding to components from the extract and then are precipitating on the glass slides. None of the extracts gave any signal with the antibodies spotted on the glass slide.

III. Additional Technologies

A. Universal Antibody Binding Layer

This embodiment employs a universal and directed immobilization of antibodies on glass, plastic or any other type of surfaces for a consequent use in detection of proteins and other antigens in high-throughput format.

The basic principle is to utilize proteins and ligands with affinity towards antibodies (including but not limited to Protein A, Protein G, Protein L, Protein LA) which are covalently immobilized to a glass, plastic or any other type of surfaces. After the immobilization of the affinity ligands the antibodies are deposited on the same locations and reversibly immobilized. The affinity ligands thus form a layer which protects the consequently bound antibodies from detrimental surface effects. Additional benefit is the directed mode of immobilization as compared to that of direct covalent attachment of the antibodies to activated surfaces. This results in 100% availability of the antigen binding sites on the antibodies for consequent detection of antigens. It also provides universal conditions for binding, since the formation of ligand/antibody complex is obtained under mild physiological conditions where as covalent immobilization of proteins is often performed under conditions that might be detrimental to their biological activity.

The surfaces that are to be used for the antibody array are activated by common chemical means (glass surfaces are aminated by means of silanization). The amino groups on the surface are activated by common chemical reactions (such as reaction with 1,4-Phenylene-diisothiocyanate (PDITC)). Affinity ligand (Protein A for an example) is solubilized in a buffer appropriate for the covalent coupling of the ligand to the activated surface (in case of PDITC activated surface such a buffer might have the composition: 0.1 M sodium carbonate pH 9.4 containing 1% Glycerol). The solubilized affinity ligand is deposited by various means on the activated surface and the spots containing the affinity ligand are left to dry.

A second consequent deposition of antibodies is performed over the locations of the covalently attached affinity ligand. Since the affinity ligand possesses broad specificity towards various types of antibodies, a number of different antibodies can be immobilized reversibly in an array format on the surface.

B. Sandwich Labeling Protocol

In these embodiments, the principle of immunoprecipitation is employed by utilizing an array of monoclonal antibodies (immobilized on the surface by means of covalent or affinity attachment) for the initial primary adsorption of the corresponding antigen. The excess antigen is immobilized to the primary binding sites by formation of immunoprecipitation complexes with a secondary polyclonal or monoclonal antibodies with specificity towards different portions of the antigen molecule. The antibodies utilized for the secondary binding are labeled in a mixture by chemical or photoreactive reaction with a proper label.

The method utilizes the principle of immunoprecipitation by utilizing an array of monoclonal antibodies (immobilized on the surface by means of covalent or affinity attachment) for the initial primary adsorption of the corresponding antigen. For an example, pure antibodies or antibody fragments are immobilized by covalent attachment on PDITC activated glass or on glass surface coated with Protein A, G or LA. The residual active groups on the surface used for immobilization are blocked by a proper agents (dry milk or BSA solutions).

The whole cell extracts can be applied directly to the arrayed antibodies and after short incubation a predetermined amount of the labeled secondary antibody mixture. The excess antigen is immobilized to the primary binding sites by formation of immunoprecipitation complexes with the labeled secondary antibodies. Another option is to mix the whole cell extracts with the so-called labeled secondary antibody mixture and apply this mixture to the primary antibodies arrayed on the surface. This gives the opportunity to utilize different labels for different types or sources of tissue. For an example, if one type of tissue extract is incubated with the antibody mixture labeled with Cy3 and the second type of tissue extract is incubated with the same quantity and composition of antibody mixture labeled with Cy5 fluorescent dye, one can mix these two differentially labeled extracts and apply the mixture to arrayed primary antibodies. The difference of the signal from Cy3 and Cy5 label will correspond to the difference in expressed antigen (differential expression analyses of proteins for an example of healthy and diseased tissue).

The benefits of the proposed method are as follows:

1) The labeling procedure of antibodies and/or antibody mixtures can be carried under universal conditions as compared to labeling of whole cell extracts.
2) The specificity and selectivity of detection will be increased due to the fact that signal can be detected only if the antigen is present in intact form that contains at least two antigenic sites (in case of using a monoclonal antibody as a secondary labeled component) or even multiple antigenic sites (in case of the use of multiple monoclonal or polyclonal antibody as a secondary labeled component).
3) Additional benefit will be the possibility to utilize the information from the immunoprecipitation complex formed by the use of multiple monoclonal or polyclonal antibody as a secondary labeled component of the state of antigen degradation—i.e. the more intact antigen molecules, the higher the detected signal will be. In addition labeling of monoclonal antibodies with specificity towards different antigenic sites with different labels and their use as a secondary binding component will provide information on the regions of degradation.
4) The amount of bound antigen and hence the signal is amplified due to the formation of 3D immunoprecipitation complex containing multiple copies of labeled secondary antibody.

Furthermore:

1. Use of a pool of pre-labeled second antibodies with affinities for different epitopes on the antigens.
   possibility for amplification of the signal by the use of polyclonal antibodies at tertiary binding events (if counting the immobilization of the primary antibody as primary binding event)
   possibility to perform a homogeneous binding assay between the labeled antibody pool and non modified sample (extract) followed by detection of the immunocomplexes by binding to the primary immobilized antibodies.
   added simplicity and robustness of this approach—decrease of time for preparation of extracts, generic method for labeling of antibodies, premixed antibodies are additional reagent that has to be purchased, less troubleshooting C. Fractionation In this embodiment, a pool of covalently attached antibodies, e.g., one or more columns of antibodies, is employed for enrichment of antigens from whole cell extracts. After reversible adsorption of the antigens on the multi-antibody column, the non adsorbed material is washed away with washing buffer and the specifically retarded antigens are eluted and collected for further labeling and incubation with antibody array containing the same antibodies that were used for initial enrichment.

Two multiaffinity columns containing the same antibodies that are immobilized on the glass surface are developed. One of the columns contains antibodies against low abundant antigens and is loaded with larger quantity of the cellular extract. The second column contains antibodies against the highly abundant antigens and is loaded with smaller quantity of the cellular extract. In total the kit contains 4 columns—two each for preparation of Cy3 and Cy5 labeled samples. Approximately 2.5 µg of each antibody is used per column. After washing of non adsorbed components the adsorbed antigens will be eluted from the multiaffinity columns, labeled and incubated with the antibody array.

The benefits of this approach are:

a. Significant decrease of the complexity of the analyte.
b. Expected low background—so far with mixes of up to 20 labeled antigens we are able to keep the background to the required minimum.
c. One could avoid lengthy exposure of the antigens at room temperature to the proteases present in whole cell extracts—the labeling procedure will be carried out after the preliminary fractionation which in principle should decrease significantly the proteolytic activity in the enriched sample.

D. Subtraction Signal Detection Protocol

This protocol exploits the reversible type of bonds of the immunocomplexes. It is based on the difference of signal from bound and unbound antigen. Labeling of complex biological samples (such as these from whole cell extracts) is a cumbersome and difficult task and reliable procedures are not available. There are numerous reasons for that, such as reproducibility in the sample composition from extract to extract, as well as the presence of proteolytic enzymes that change the components of the sample during extraction and especially during labeling, which has to be carried often for extended periods of time at ambient temperature. This invention addresses some of these issues by performing the labeling procedure on already purified sample that is depleted from proteins and proteases for which there are no specific antibodies in the adsorption matrix. The idea is to immobilize antibodies against the proteins that will be analyzed, followed by extraction of the sample containing the analyte. This sample is incubated without further modification with the surface containing the immobilized antibodies. The non adsorbed proteins are washed out and the immunocomplexes are labeled with monofunctional molecule carrying a signal moiety. The excess of labeling molecule is washed away and the signal which is a composite of the signals carried both by the antibodies and the bound antigens are measured out. Then the immunocomplexes are disrupted and the labeled antigens are washed away and the residual signal is measured. The difference of the signal obtained before and after the removal of the antigen is a measure for the quantity of labeled antigen and hence the quantity of the antigen in the sample. The residual signal from the labeling of the antibodies can be reduced by pretreatment of the immobilized antibodies with a chemistry that blocks their primary amino groups. By utilizing a series of dilutions of each antibody one can increase the sensitivity of the analysis.

E. Use of photoreactive Biotin for labeling of the whole cell extracts, followed by incubation with Cy3/Cy5 labeled avidin (or with HRP/AP labeled avidin for membrane antibody array).

IV. Additional Results

A. We have successfully achieved detection of antigens from whole cell extracts.

Figure 15A:
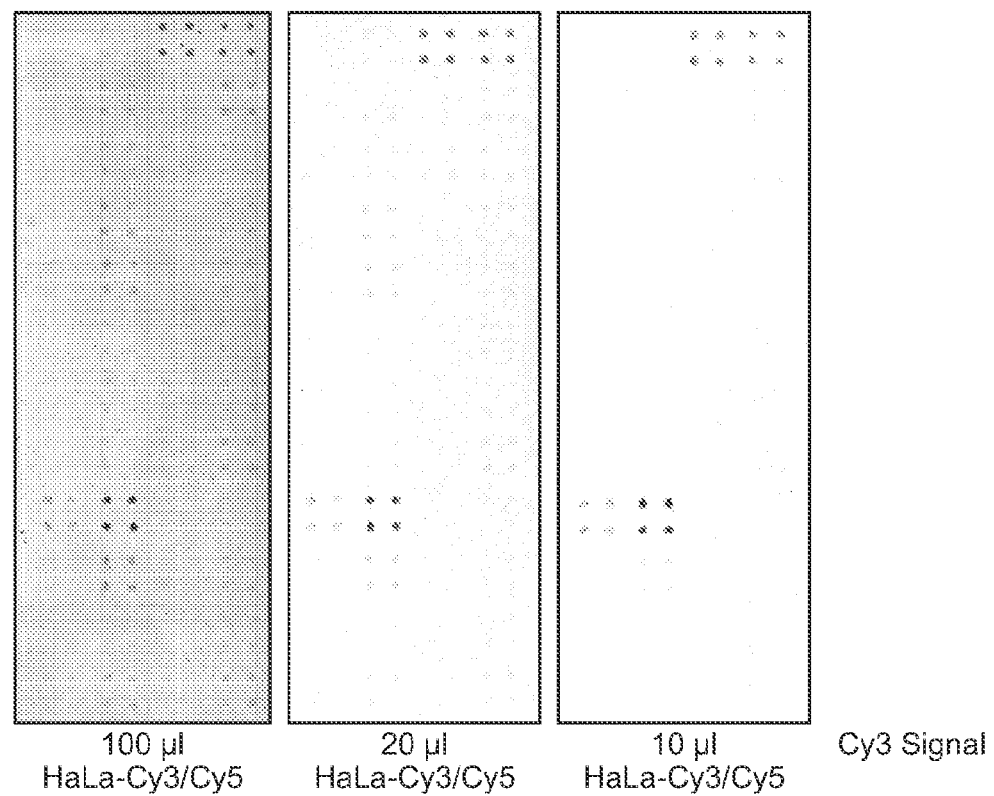
FIGS. 15A and 15B provide the results obtained with assays of whole cell extracts.
Figure 15B:
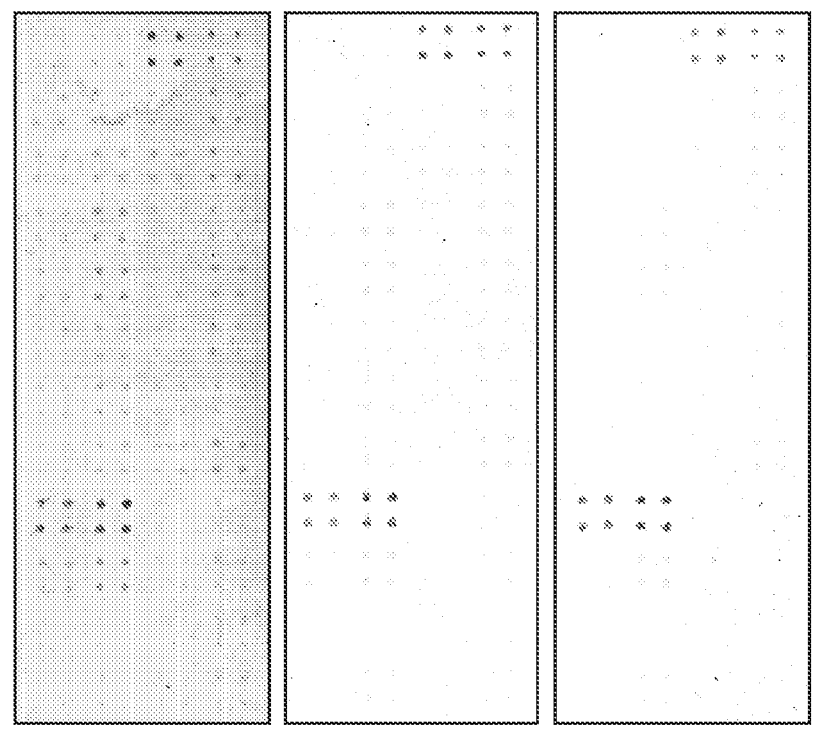

Using the antibody array described above, HeLa cell extracts labeled with either Cy3 or Cy5 were assayed according to the following conditions. FIG. 15A-B*locking*: 1% dry milk in TST-1 h; Storage, 1% Glycerol in TST 4° C.; Incubate: TST: 1% Dry Milk; 5% pluronic 68; 0.2% apple pectin; Sample 1 µl GFP-Cy3/Cy5, 1 µl AdvanTaq-Cy3/Cy5+ respective HeLa. FIG. 15B-B*locking*: 1% dry milk in sodium carbonate pH9.3-1 h; Storage, 1% Glycerol in TST 4° C.; Incubate: TST:1% Dry Milk; 5% pluronic 68; 0.2% apple pectin; Sample 1 µl GFP-Cy3/Cy5, 1 µl AdvanTaq-Cy3/Cy5+ respective HeLa.

B. We have shown that preliminary enrichment is possible by synthesizing multi-antibody adsorbent and increasing of the concentration of some of the antigens.

Figure 16:
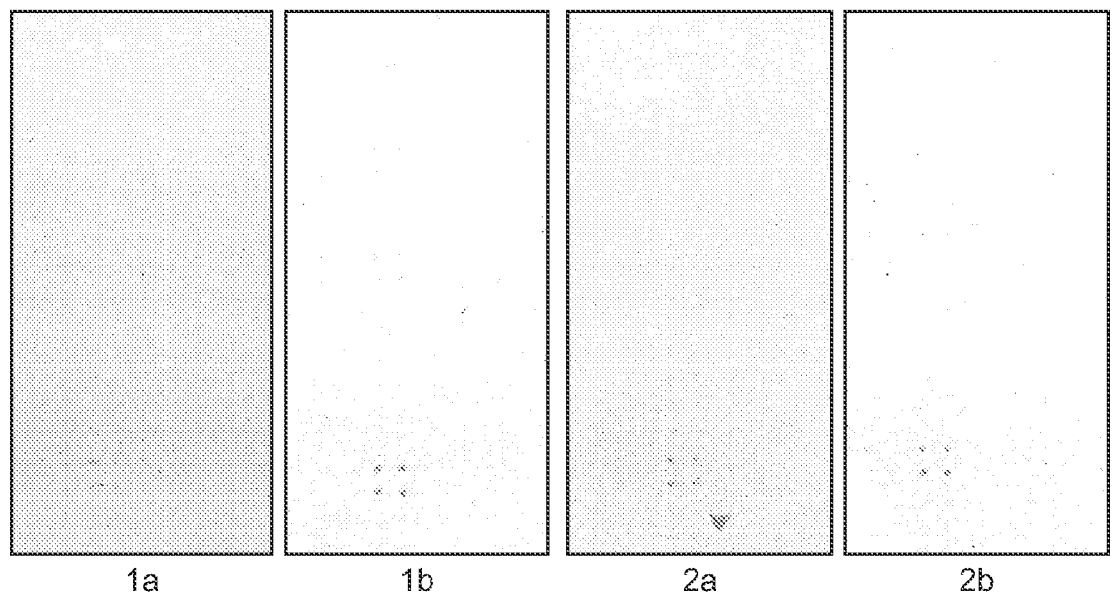
FIG. 16 shows the results obtained with using an antibody column prefractionation protocol.

FIG. 16 shows this multi-antibody column effect. In FIG. 16, 500 µl of whole HeLa cell extract (1a & 1b) and 100 µl of whole cell HeLa biotinylated extract (2a & 2b) (250 and 125 µg total protein) were loaded on two 0.1 ml samples of adsorbent containing antibodies against human signaling proteins. The non adsorbed material from each sample was applied to glass slides containing the same immobilized antibodies (1a and 2a), while the adsorbed material was eluted from the adsorbents and applied to two new glass slides with the same immobilized antibodies. Detection was performed with Cy3/Cy5 labeled avidin. Only the Cy3 channel signal is shown. At least one of the antigens was enriched significantly and the background is reduced also significantly which improves the detection range.

Figure 17A:
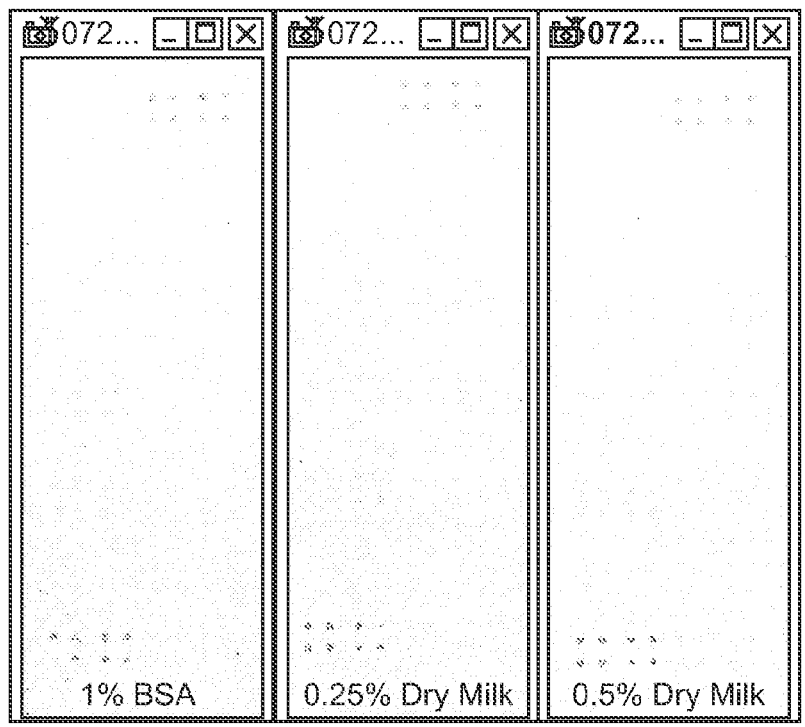
FIGS. 17A and B show the results obtained with using a sandwich labeling protocol.
Figure 17B:
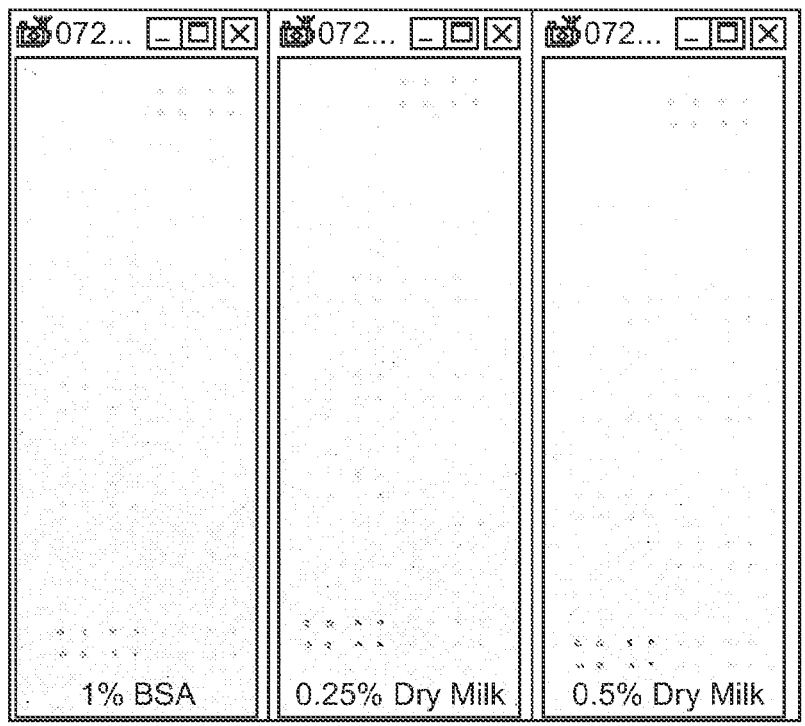

C. We have shown that a sandwich type detection is possible (capture Ab, followed by biotinylated antigen, followed by second antibody labeled with biotin, followed by Cy3 labeled avidin). In FIG. 17A, a protocol employing 1 ng of all antigens+1 µl of Cy3 & Cy5 GFPuv and biotinylated AdvanTaq followed by sCy3/Cy5-Avidin was employed. In FIG. 17B, a protocol employing 4 ng of all antigens+1 µl of Cy3 & Cy5 GFPuv and biotinylated AdvanTaq followed by Cy3/Cy5-Avidin was employed.

V. Array Preparation

A. Glass Slides Activation 20 glass microscope slides having the following dimensions 25×76 mm (Type 1, BD Clontech) were activated by incubating the slide with DVS solution (1M Sodium Carbonate—$Na_2CO_3$+4 mL of DVS) for 30 min at ambient temperature. The slides were then washed 3× with Milli Q-$H_2O$. The slides were then dried by centrifugation for 25 min at 2000 rpm. The dried activated slides were stored in vacuum desiccator.

B. Array Printing

The monoclonal antibodies to the antigens listed in the Antibody Table above, all provided by BD Pharmingen, were printed onto the surface of the activated glass slide produced in I.A. to produce an antibody array. Printing was as follows:

1. For each antibody, a fluid binding reagent composition was prepared as follows:

1 µl of Ab (7.0 mg/mL)+9 µl of buffer (0.1 M NaHCO$_3$; 0.1% Dextran 35K); 4% Na$_2$SO$_4$; pH 9.3).

2. Each antibody composition was deposited onto the array surface using a Cartesian Technologies MicroSys arrayer with 16 ChipMaker #2 pins. Each antibody was printed in duplicates. The technical specs of the pins state that they deposit between 5 and 10 mL of liquid per spot. After printing the first 16 antibodies the pins were washed with deionized water and 96% ethanol and dried on vacuum. Next 16 antibodies were deposited in the same manner. Up to 512 different antibodies for a total of 1024 spots.

3. Blocking

The array resulting from 1.B.2. was blocked with 1% BSA in TST (0.075% Tween 20) pH 7.4 overnight 4° C.

4. Storage

The resultant array was stored in 50% Glycerol/50% TST (0.075% Tween 20) pH 7.4 at 20° C. Our stability data shows that after 6 months of storage there was approximately 80% of the residual activity as determined by comparison of the signal of freshly printed and stored glass slides.

II. Assay

A. Sample preparation Cell pellets or tissue samples of approximately 50 mg are the minimal starting amount. The amount of each sample for comparison is determined. The samples are frozen down in liquid nitrogen or −80° C. freezer. Twenty volumes of extraction/labeling buffer (0.1 M NaHCO3, 0.8% n-Octyl-β-D-Glucopyranoside (ODG), 0.2% NP-40 pH 8.3) to cell weight are added to each sample. The cells are mixed into homogeneous suspension with the extraction/labeling buffer and then mixed slowly for 10 minutes at room temperature, The suspension is centrifuged for 30 minutes at 10000×g and 4° C. The supernatant is collected and the protein concentration of the two samples is determined by BCA protein analyses.

B. Labeling (The following is the dual color detection protocol. The single color (biotinylation) protocol is similar, but it involves labeling of only 2 samples in two reactions. There is an additional step in the single color detection—the incubation of bound antigens on the slide with Cy3 or Cy5-avidin or streptavidin). Both protein extracts (Sample A and B) are diluted to 1.1 mg/mL total protein with extraction buffer to a total volume of 1.1 mL. Four 1 mL eppendorph tubes are pre-labeled Sample A-Cy3, Sample A-Cy5, Sample B-Cy3 and Sample B-Cy5 respectively. 110 µl of extraction buffer (pH 8.3) is added to a tube containing dry Cy3-Dye (Amersham Pharmacia) and the contents are mixed thoroughly for 20 seconds to suspend all the dye in tube. The tube is centrifuged shortly for 10 seconds to pool down the dye solution. 50 µl of Cy3 dye solution is added to each of the two Sample A-Cy3 and Sample B-Cy3 pre-labeled eppendorph tubes. The same procedure is repeated by splitting the Cy5 dye solution into the Sample A-Cy5 and Sample B-Cy5 eppendorph tubes respectively.

450 µl of Sample A is added to the Sample A-Cy3 tube containing Cy3-dye and another 450 µl of Sample A to the Sample A-Cy5 tube containing Cy5-dye. 450 µl of Sample B is added to the Sample B-Cy3 tube containing Cy3-dye and another 450 µl of Sample A to the Sample B-Cy5 tube containing Cy5-dye.

The solutions are mixed well by inverting 3 times the tube and the contents are centrifuged down shortly for 10 seconds.

The labeling reaction is carried out for 1 hour and 30 minutes at 4° C., including mixing by inverting the tube approximately every 20 minutes.

4 ul of Blocker is added to each tube and the suspensions are incubated for additional 30 minutes, mixing each sample every 10 minutes.

Four PD-10 columns (Amersham Pharmacia) are labeled Sample A-Cy3, Sample A-Cy5, Sample B-Cy3 and Sample B-Cy5 respectively.

Four collection 2 mL eppendorph tubes are labeled DSample A-Cy3, DSample A-Cy5, DSample B-Cy3 and DSample B-Cy5 respectively.

The equilibration of the four PD-10 columns is performed with 3×5 ml of desalting buffer (10 mM Tris, 0.15 M NaCl, 0.075% Tween 20; 0.8% ODG; 0.2% NP-40 pH 7.4) (DSample X stands for Desalted Sample X, where X is either A or B). The 504 µl of the labeled extracts after the completion of the blocking named Sample A-Cy3, Sample A-Cy5, Sample B-Cy3 and Sample B-Cy5 are desalted into their corresponding columns.

The desalted samples are collested in the pre-labeled tubes with 2.0 mL desalting buffer—each into their corresponding collection tubes. The collected samples (DSample A-Cy3, DSample A-Cy5, DSample B-Cy3 and DSample B-Cy5) are kept on ice.

The protein concentration and the substitution degree with the respective dye is determined −60 kD is assumed as an average molecular weight of the proteins inside each sample unless there is a prior knowledge of the molecular weight distribution of the proteins (the concentration should be approximately 0.2 mg/mL, substitution degree between 2 and 4 is preferable).

C. Incubation The side walls of four chambers of the an incubation bath are marked with Slide#1—Incubation, Slide#1—Wash, Slide#2—Incubation and Slide#2—Wash respectively.

5 mL of incubation buffer (10 mM Tris; 0.2% Pectin; 150 mM NaCl; 5% Tween 20; 5% Pluronic 69 pH 7.4) is added in the four chambers of the incubation bath. Two eppendorph tubes are marked with the inscriptions Slide#1 Mix and Slide#2 Mix respectively.

100 µg of Sample A-Cy5 and Sample B-Cy3 is mixed in the tube labeled Slide#1 Mix.

100 µg of Sample A-Cy3 and Sample B-Cy5 is mixed in the tube labeled Slide#2 Mix.

Equal amounts of protein from tubes Slide#1 Mix and Slide#2 Mix in the range between 10 and 50 µg protein is added to the chambers labeled Slide#1—Incubation and Slide#2—Incubation respectively. 20 µl of 1% SDS is added to each sample.

The samples are pre-incubated under slow mixing for 30 minutes.

The two supplied slides are washed three times with stock incubation buffer inside the storage chamber.

The slides are moved with their labels facing upside in the chambers containing the samples (Slide#1—Incubation and Slide#2—Incubation respectively) and incubated with the sample for 30 min.

D. Washing

The slides are washed for 5 minutes each by bringing the slide out and down the chamber five times to allow liquid exchange under the slide with micro tip from a pipette. The wash is performed with the following solutions:

Incubation buffer by transferring the slides to the chambers labeled Slide#1—Wash and Slide#2—Wash respectively.

Wash buffer #1 (10 mM Tris; 0.5 M NaCl; 5% Tween 20 pH 7.4)

Wash buffer #2 (10 mM Tris; 0.15 M NaCl; 5% Tween 20 pH 7.4)

Wash buffer #3 (10 mM Tris; 0.15 M NaCl; 5% Tween 20; 0.1% PEI (SIGMA# P3143) pH 7.4)

Wash buffer #4 (10 mM Tris; 0.15 M NaC; 2% Tween 20; 0.1% PEI pH 7.4)

Wash buffer #5 (10 mM Tris; 0.15 M NaCl; 1% Tween 20 pH 7.4)

Wash buffer #6 (15 mM sodium citrate; 150 mM NaCl; 1% Tween 20 pH 7.0)

Wash buffer #7 (10 mM Tris; 0.15 M NaCl; 0.2% Tween 20 pH 7.4)

The slides are dried by centrifugation for 20 min at 2000×g and room temperature.

E. Detection

Pre-scan at lower resolution is used to determine the optimal power and detector sensitivity in order to minimize photobleaching of the fluorescent dyes.

The slides are scanned immediately at the optimal settings for the scanner. The analytical software of any choice is used to determine the signal from each dye for each antibody-antigen pair from both slides. The Cy5/Cy3 ratios for each antibody-antigen pair are determined from both slides.

The two ratios (Slide#1 and Slide#2 respectively) are tabulated against the names of the antigen names.

The Ratio of the Ratios from the two slides is determined. The square root of this Ratio of the Ratios is the Internally Validated Ratio (IVR) coefficient that can be used as any normal coefficient for evaluation of abundance difference of given antigen in the two samples.

There are different opinions on what constitutes a valid change in the protein level. For a difference of 1.5 and more in a given protein between Sample A and Sample B the IVR has to be higher than 1.5 or lower than 0.66.

For a difference of 2 and more in a given protein between Sample A and Sample B the IVR has to be higher than 2 or lower than 0.5.

Once the valid changes are determined, the Signal/Background ratios for these antibody-antigen pairs is analysed. Only IVR for antibody-antigen pairs with Signal/Background ratios that are higher than 2 can be considered as valid.

F. Results a. Sensitivity

Model mixes of 10 different antigens in different relative amounts were labeled, desalted and incubated against each other as described above.

Figure 18:
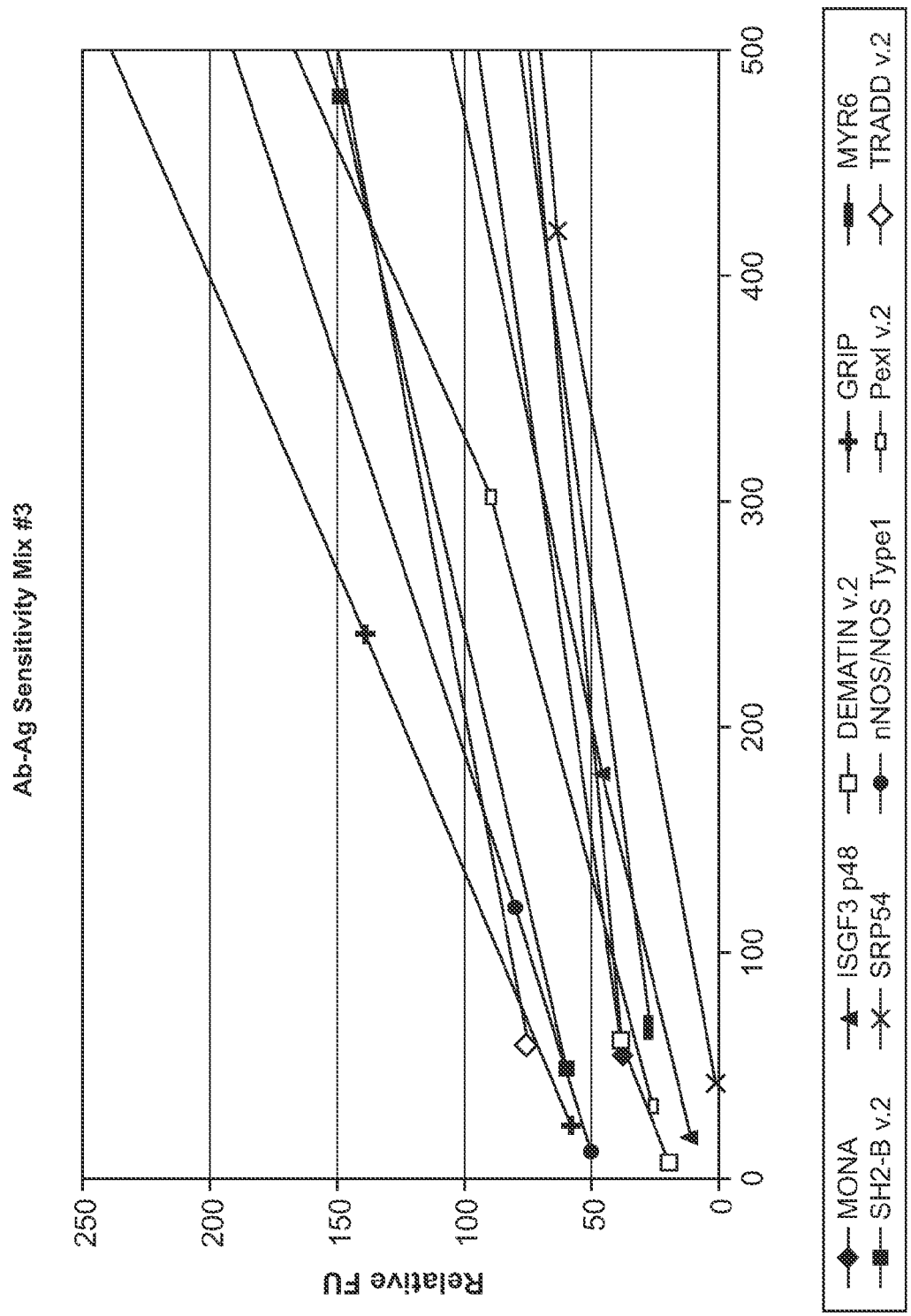
FIG. 18 provides a graphical result of an antibody array assay described in the experimental section, below.

Below is the tabulated data of these experiments. The Table presents the theoretical and experimentally obtained Ratio of Ratios and IVR coefficients. As one can see there is a very good correlation between the theoretical and experimental values at up to 100 times dilutions for the antigen mixes covering antigen concentrations between 100 pg/mL and 60 ng/mL. FIG. 18 presents the signals obtained for one of the mixes.

| | | | | | | | | | | |
|---|---|---|---|---|---|---|---|---|---|---|
| | | | Ag Mix Dilutions | | | | | | | |
| | R/R | | Dilution | | | IVR | | Dilution | | |
| 1 vs 2 | Theor. | 1 | 10 | 100 | 1000 | Theor. | 1 | 10 | 100 | 1000 |
| MONA | 0.11 | 0.13 | 0.18 | 0.32 | 0.80 | 0.33 | 0.37 | 0.42 | 0.57 | 0.89 |
| ISGF3 p48 | 9.00 | 8.53 | 7.73 | 5.48 | 3.55 | 3.00 | 2.92 | 2.78 | 2.34 | 1.88 |
| DEMATIN v.2 | 4.84 | 3.11 | 3.71 | 3.59 | 3.41 | 2.20 | 1.76 | 1.93 | 1.90 | 1.85 |
| GRIP | 16.00 | 8.08 | 12.07 | 5.65 | 2.98 | 4.00 | 2.84 | 3.47 | 2.38 | 1.73 |
| MYR6 | 0.02 | 0.11 | 0.09 | 0.22 | 0.86 | 0.14 | 0.33 | 0.30 | 0.47 | 0.93 |
| SH2-B v.2 | 0.16 | 0.27 | 0.26 | 0.28 | 0.49 | 0.40 | 0.52 | 0.51 | 0.52 | 0.70 |
| SRP54 | 0.21 | 0.18 | 0.15 | 0.35 | 0.94 | 0.45 | 0.43 | 0.38 | 0.59 | 0.97 |
| nNOS/NOS Type1 | 6.25 | 3.42 | 4.03 | 3.61 | 2.39 | 2.50 | 1.85 | 2.01 | 1.90 | 1.55 |
| Pex1 v.2 | 49.00 | 25.52 | 22.82 | 11.34 | 3.16 | 7.00 | 5.05 | 4.78 | 3.37 | 1.78 |
| TRADD v.2 | 0.06 | 0.27 | 0.07 | 0.19 | 1.03 | 0.25 | 0.52 | 0.27 | 0.44 | 1.02 |
| | R/R | | Dilution | | | IVR | | Dilution | | |
| | Theor. | 1.00 | 10.00 | 100.00 | 1000.00 | Theor. | 1.00 | 10.00 | 100.00 | 1000.00 |
| 3 vs 1 | | | | | | | | | | |
| MONA | 9.00 | 9.90 | 8.16 | 6.83 | 3.44 | 3.00 | 3.15 | 2.86 | 2.61 | 1.85 |
| ISGF3 p48 | 0.11 | 0.16 | 0.14 | 0.21 | 0.29 | 0.33 | 0.39 | 0.38 | 0.46 | 0.54 |
| DEMATIN v.2 | 0.01 | 0.01 | 0.02 | 0.04 | 0.09 | 0.09 | 0.12 | 0.13 | 0.21 | 0.29 |
| GRIP | 0.25 | 0.57 | 0.43 | 0.56 | 0.56 | 0.50 | 0.76 | 0.65 | 0.75 | 0.75 |
| MYR6 | 121.00 | 17.66 | 25.27 | 10.08 | 1.78 | 11.00 | 4.20 | 5.03 | 3.17 | 1.34 |
| SH2-B v.2 | 4.00 | 3.65 | 3.43 | 3.15 | 2.39 | 2.00 | 1.91 | 1.85 | 1.78 | 1.54 |
| SRP54 | 1.96 | 1.92 | 1.88 | 1.67 | 0.38 | 1.40 | 1.39 | 1.37 | 1.29 | 0.62 |
| nNOS/NOS Type1 | 0.04 | 0.10 | 0.11 | 0.10 | 0.38 | 0.20 | 0.32 | 0.33 | 0.32 | 0.62 |
| Pex1 v.2 | 0.51 | 0.53 | 0.62 | 0.67 | 0.89 | 0.71 | 0.73 | 0.79 | 0.82 | 0.94 |
| TRADD v.2 | 25.00 | 6.91 | 23.78 | 4.81 | 2.09 | 5.00 | 2.63 | 4.88 | 2.19 | 1.45 |
| 3 vs 2 | | | | | | | | | | |
| MONA | 1.00 | 1.38 | 2.06 | 1.68 | 1.37 | 1.00 | 1.18 | 1.43 | 1.30 | 1.17 |
| ISGF3 p48 | 1.00 | 1.40 | 1.90 | 1.78 | 1.14 | 1.00 | 1.18 | 1.38 | 1.33 | 1.07 |
| DEMATIN v.2 | 0.04 | 0.03 | 0.08 | 0.09 | 0.76 | 0.20 | 0.18 | 0.29 | 0.30 | 0.87 |

-continued

| | Ag Mix Dilutions | | | | | | | | | |
|---|---|---|---|---|---|---|---|---|---|---|
| GRIP | 4.00 | 5.21 | 5.61 | 4.18 | 1.66 | 2.00 | 2.28 | 2.37 | 2.04 | 1.29 |
| MYR6 | 2.47 | 2.51 | 2.57 | 2.75 | 1.35 | 1.57 | 1.59 | 1.60 | 1.66 | 1.16 |
| SH2-B v.2 | 0.64 | 1.02 | 1.11 | 1.43 | 1.12 | 0.80 | 1.01 | 1.06 | 1.20 | 1.06 |
| SRP54 | 0.40 | 0.29 | 0.63 | 0.58 | 1.66 | 0.64 | 0.54 | 0.79 | 0.76 | 1.29 |
| nNOS/NOS Type1 | 0.25 | 0.43 | 0.45 | 0.50 | 0.57 | 0.50 | 0.65 | 0.67 | 0.71 | 0.75 |
| Pex1 v.2 | 25.00 | 21.23 | 14.07 | 6.93 | 1.99 | 5.00 | 4.61 | 3.75 | 2.63 | 1.41 |
| TRADD v.2 | 1.56 | 2.41 | 2.86 | 1.20 | 1.09 | 1.25 | 1.55 | 1.69 | 1.10 | 1.05 |

It is evident from the above results and discussion that the subject invention provides an important advance in the field of proteomics. Specifically, the subject invention provides for a rapid and high throughput manner to simultaneously determine quantitatively the amount of large number of proteins in sample with a high sensitivity for even the lowest concentration proteins. In addition, the subject methods can be used with the wide variety of sample types, including crude cell extracts. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to a antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of determining whether a sample includes at least one analyte of interest, said method comprising:
   (a) contacting said sample with an array of a plurality of distinct binding agents displayed on a surface of a solid support, wherein said sample is contacted with said array in the presence of a metal ion chelating polysaccharide and each of said binding agents at least comprises a specific epitope binding domain of an antibody;
   (b) detecting the presence of any resultant binding complexes on said surface to obtain analyte binding data; and
   (c) employing said analyte binding data to determine whether said sample includes said at least one analyte of interest;
wherein said method provides a sensitivity of at least 10 pg/ml of analyte of interest when said analyte is directly fluorescently labeled.

2. The method according to claim 1, wherein said metal ion chelating polysaccharide comprises polygalactouronate domains.

3. The method according to claim 2, wherein said metal ion chelating polysaccharide is a pectin.

4. The method according to claim 3, wherein said pectin is apple pectin.

5. The method according to claim 1, wherein said method further comprises extracting said at least one analyte from a cellular source and labeling said extracted at least one analyte, wherein said extracting and labeling steps employ the same buffer composition.

6. The method according to claim 5, wherein said buffer composition is free of components that include primary amine moieties.

7. The method according to claim 6, wherein said buffer composition has a pH ranging from about 7 to about 12.

8. The method according to claim 7, wherein said buffer composition is capable of extracting at least about 95% of the proteins of an initial cellular source.

9. The method according to claim 1, wherein said at least one analyte is a protein.

10. The method according to claim 1, wherein said method comprises determining the presence of at least two distinct analytes in said sample.

11. The method according to claim 1, wherein said method comprises a plurality of washing steps between said contacting and detecting steps.

12. The method according to claim 1, wherein:
   (a) said method comprises quantitatively detecting at least two different protein analytes in said sample; (b) said method further comprises extracting said at least one analyte from a cellular source and labeling said extracted at least one analyte, wherein said extracting and labeling steps employ the same buffer composition; and (c) wherein said method comprises a plurality of washing steps between said contacting and detecting steps.

13. The method according to claim 12, wherein said metal ion chelating polysaccharide comprises polygalactouronate domains.

14. The method according to claim 13, wherein said metal ion chelating polysaccharide is a pectin.

15. The method according to claim 14, wherein said pectin is apple pectin.

16. The method according to claim 12, wherein said method is a method of determining a protein expression profile for said sample.

17. The method according to claim 1, wherein said method further comprises a sample fractionating step prior to said contacting step.

18. The method according to claim 17, wherein said fractionating step comprises contacting said sample with at least one affinity column.

* * * * *